United States Patent
Leduc et al.

(10) Patent No.: US 10,159,517 B2
(45) Date of Patent: Dec. 25, 2018

(54) BONE PLATE WITH ATTACHABLE WEDGE

(71) Applicant: Stryker European Holdings I, LLC, Kalamazoo, MI (US)

(72) Inventors: Stephane Leduc, Laval (CA); Marcel Abt, Solothurn (CH); Martin Felder, Niederbipp (CH); Markus Wittwer, Langendorf (CH); Oliver Ammann, Bern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 556 days.

(21) Appl. No.: 14/793,215

(22) Filed: Jul. 7, 2015

(65) Prior Publication Data

US 2016/0000486 A1 Jan. 7, 2016

Related U.S. Application Data

(60) Provisional application No. 62/021,376, filed on Jul. 7, 2014.

(51) Int. Cl.
*A61B 17/80* (2006.01)

(52) U.S. Cl.
CPC .............................. *A61B 17/8095* (2013.01)

(58) Field of Classification Search
CPC ................................................. A61B 17/8095
See application file for complete search history.

(56) References Cited

U.S. PATENT DOCUMENTS

| | | | |
|---|---|---|---|
| 5,620,448 A | 4/1997 | Puddu et al. | |
| 5,749,875 A | 5/1998 | Puddu | |
| 5,766,251 A | 6/1998 | Koshino | |
| 6,008,433 A | 12/1999 | Stone | |
| 6,203,546 B1 | 3/2001 | MacMahon | |
| 6,235,059 B1 | 5/2001 | Benezech et al. | |
| 6,303,136 B1 | 10/2001 | Li et al. | |
| 6,823,871 B2 | 11/2004 | Schmieding | |
| 6,837,905 B1 | 1/2005 | Lieberman | |
| 7,803,157 B2 | 9/2010 | Michelson | |
| 8,690,944 B2 | 4/2014 | Bonutti | |
| 9,198,768 B1* | 12/2015 | Pisharodi | A61F 2/4425 |
| 2008/0051799 A1 | 2/2008 | Bonutti | |
| 2009/0177203 A1 | 7/2009 | Reiley | |

(Continued)

FOREIGN PATENT DOCUMENTS

EP   1308135 A2   5/2003

OTHER PUBLICATIONS

Konigsee, Winkelstabile HTO-Plate, Angle Stable HTO-Plate, Published as of 2005.

(Continued)

*Primary Examiner* — Olivia C Chang
(74) *Attorney, Agent, or Firm* — Lerner, David, Littenberg, Krumholz & Mentlik, LLP

(57) ABSTRACT

An implant for use in an open-wedge osteotomy, the implant comprising a plate including a first end and a second end, a first screw hole adjacent the first end, a second screw hole adjacent the second end, and at least one track having a first width disposed between the first and second screw holes; and a wedge body having an engagement portion that is passed through at least the first width of the at least one track so as to movably engage the wedge body with the plate.

18 Claims, 21 Drawing Sheets

(56) References Cited

U.S. PATENT DOCUMENTS

| | | |
|---|---|---|
| 2009/0234359 A1 | 9/2009 | Onoue et al. |
| 2012/0184959 A1 | 7/2012 | Price et al. |
| 2014/0005728 A1 | 1/2014 | Koay et al. |
| 2017/0035479 A1* | 2/2017 | Paik ................ A61B 17/80 |

OTHER PUBLICATIONS

Aesculap, Position HTO System Brochure, Published on Jan. 16, 2012.

* cited by examiner

US 10,159,517 B2

BONE PLATE WITH ATTACHABLE WEDGE

CROSS-REFERENCE TO RELATED APPLICATIONS

The present application claims priority from provisional U.S. Patent Application No. 62/021,376, filed Jul. 7, 2014, the disclosure of which is hereby incorporated herein by reference.

BACKGROUND OF THE INVENTION

The present invention relates to improved devices, methods, and kits for use in open-wedge osteotomy procedures in which the communication between a wedge member and a plate member allows for compatibility with a wider range of patient anatomies and greater ease of use for implantation.

An osteotomy is a surgical procedure whereby a bone is cut to shorten, lengthen, or change its alignment. It may be performed to correct deformities such as a hallux valgus, a progressive forefoot deformation, or to relieve pain from arthritis, especially in the hip or knee. The procedure usually entails either: the removal of a typically wedge-shaped portion of a bone by cutting perpendicular to the long axis of the bone, whereupon the bone may be "closed," i.e., fused together at the space and allowed to heal; or a simple partial cut perpendicular to the long axis, whereupon the bone may be "opened" and fixated with an appropriate device. For example, an implant may be inserted into the space, or a bone plate may be affixed to the bone adjacent to the space, to maintain or increase the space. The "closing" or "opening" changes the spatial relationship between the remaining portions of the bone in order to adjust its alignment or length.

Open-wedge osteotomy refers to a specific type of osteotomy procedures in which a partial cut perpendicular to the long axis of the bone is made and opened subsequently. The correction is maintained by using an appropriate fixation device such as, for example, a plate with screws. Additionally, a wedge or bone graft can be added to fill the space that is opened so that the bone may return to a load-bearing state and also to facilitate bone healing. The implanted wedge helps to maintain the opened space by allowing the bone to transmit force to the wedge, thereby preserving the surgeon's aimed reduction or expansion of the angle of the bone. Depending on the location and type of open-wedge osteotomy, an additional fixation plate may also need to be affixed to the bone. A known method for performing the procedure includes performing a partial cut of a bone, subsequently opening the partial cut using a tool (e.g., an osteotome), inserting a wedge into the resultant space of the bone, positioning a bone plate against the wedge, and securing the plate to the bone. Depending on the location and type of osteotomy performed, an additional fixation means (e.g., a plate or staples) may further be implemented.

Current open-wedge osteotomy systems include either: a bone plate integral with a rigid, fixed wedge where the orientation of the wedge relative to the plate is predefined; a wedge that is attached to the implant with a screw; or a bone plate without a wedge. Due to many factors, including natural anatomic variations among patients and the location of an incision made for an osteotomy, a bone plate with an integral wedge is not optimal for all situations. Attaching the wedge to the bone plate with a screw offers some flexibility; however, it also requires yet another component to be implanted in the body. Furthermore, the preferences of practitioners may vary, as some prefer to implant wedge-less bone plates and others prefer to use the plates with a wedge. Therefore, a health care provider may be forced to keep a large inventory of incompatible plate and plate-wedge configurations to ensure proper placement of the bone plate; or, a surgeon might otherwise be relegated to securing the plate in a less-than optimal position.

Thus, there exists a need for improvements in open-wedge osteotomy that provide a greater variety of plate-wedge configurations.

BRIEF SUMMARY OF THE INVENTION

One aspect of the present invention is a device for performing an open-wedge osteotomy. The device preferably comprises a bone plate and a wedge implant. The bone plate may have a first end and a second end, a first hole adjacent the first end, a second hole adjacent the second end, and at least one track. Each track preferably has a first width disposed between each of the first and second holes. The wedge implant may have an engagement portion comprising a head with a stem attached to a wedge body. The head and stem preferably define a cross-section that allows the wedge implant to be movably, e.g., slidably and rotatably, engaged with the bone plate by placing the head through the track. Preferably, the wedge implant is moveably engaged with the plate without further attachment means, such as a screw.

The bone plate may include a plurality of holes, such as a plurality of screw holes and one or more conical holes adapted for insertion of a Kirschner wire (or "K-wire"). Of course, any hole in the plate may be cylindrical, conical, or any other shape adapted to receive a screw, K-wire, or like element. The wedge implant may further include an aperture extending through the head, the stem and, in some embodiments, a portion of the body to define a first engagement portion opposite of a second engagement portion. Each engagement portion described herein may be adapted to engage the track in a variety of ways. For example, a portion of the wedge implant may have a cross-sectional diameter sized to obtain an interference fit with the track.

Another aspect of the present invention is a method of performing an open-wedge osteotomy. A step of this method may comprise providing a bone plate having, for example, at least one first screw hole adjacent a first end, at least one second screw hole adjacent a second end, a track between the first and second screw holes, and a wedge implant. In some embodiments of this method, the bone plate is a guiding template adapted to permit formation of an osteotomy gap. The bone plate may have one or more marks to permit formation of a gap of a particular size. The wedge implant preferably has an engagement portion including, for example, a head connected to a stem connected to a wedge body. Further steps may comprise partially cutting the bone, thereby creating a partial cut and leaving an intact lateral cortex; and spreading of the partial cut to correct the deformity. An osteotomy gap may thereby be formed to have a first side, a second side, and a hinge. Further steps may comprise passing the engagement portion through the track of the bone plate to achieve a constructed condition, and inserting the wedge implant into the gap to achieve an implanted condition. Once in the constructed condition, further steps may comprise moving, e.g., sliding and rotating, the bone plate with respect to the wedge implant to find an optimal position of bone securement for the plate. When in the implanted condition, still further steps may comprise placing the bone plate at the optimal position of bone securement and inserting a screw through each of the first and second screw holes of the bone plate and into the bone.

In one exemplary method, the step of pushing the head of the wedge implant through the track of the bone plate is performed before the step of inserting the wedge implant into the gap. In another exemplary method, the step of pushing the head of the wedge implant through the track of the bone plate is performed after the step of inserting the wedge implant into the gap. In yet another exemplary method, the bone plate and/or wedge implant may be selected from a plurality of differently-shaped and differently-configured bone plates and wedge implants, respectively. In still yet another exemplary method, the osteotomy tool system may further comprise a K-wire, and the bone plate may further include a cylindrical or conical hole adjacent the first end adapted for receiving the K-wire. After the step of finding the optimal position of securement on the bone, the method may further include the step of inserting the K-wire through the conical hole and into the bone.

Yet another aspect of the present invention is a kit for performing an open-wedge osteotomy. An exemplary kit may comprise a plurality of implants, each having an engagement portion attached to a body; and a plurality of bone plates, each having at least one track. Each engagement portion is preferably interchangeable with each plate. Preferably, at least a first portion of the implants have wedge bodies. Each wedge body may be sized differently to permit securement of a particular bone plate to a particular bone or insertion of a particular implant in a particular osteotomy gap.

DETAILED DESCRIPTION

Although the embodiments described below and shown in the figures are directed to specific implants, open-wedge osteotomy tools, and procedures, it is to be understood that the concepts and novelty underlying the present invention could be utilized for other types of procedures, including other osteotomy procedures such as Cotton osteotomies, Evans osteotomies, high tibial osteotomies, and other open wedge osteotomies. Moreover, although described in connection with the correction of hallux valgus in the foot, the present invention has application in other areas of the human body, including the ankle, knee, hip, spine, and even maxillofacial areas, such as the jaw or chin.

Figure 1A:
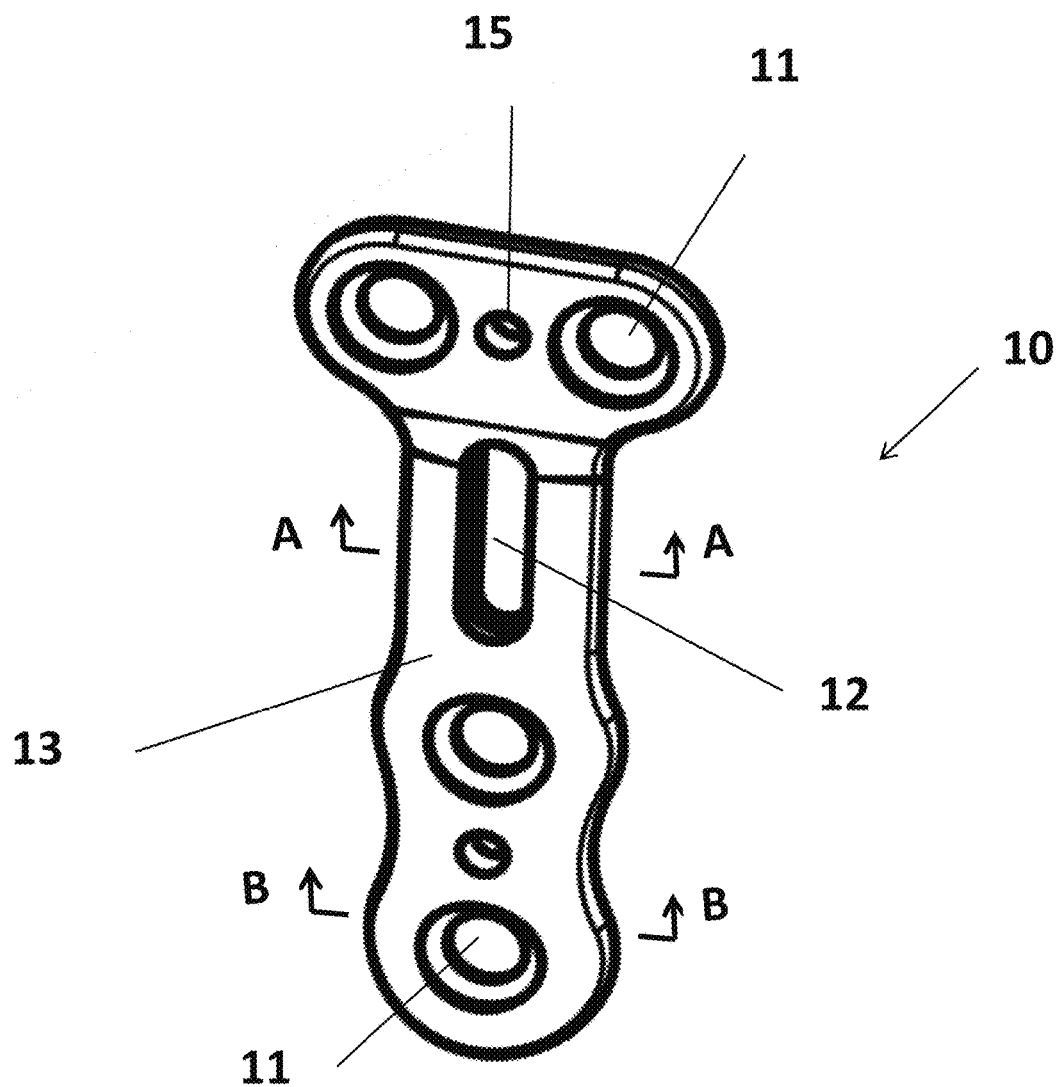
FIG. 1A is a perspective of an exemplary bone plate of the present invention.
Figure 1B:
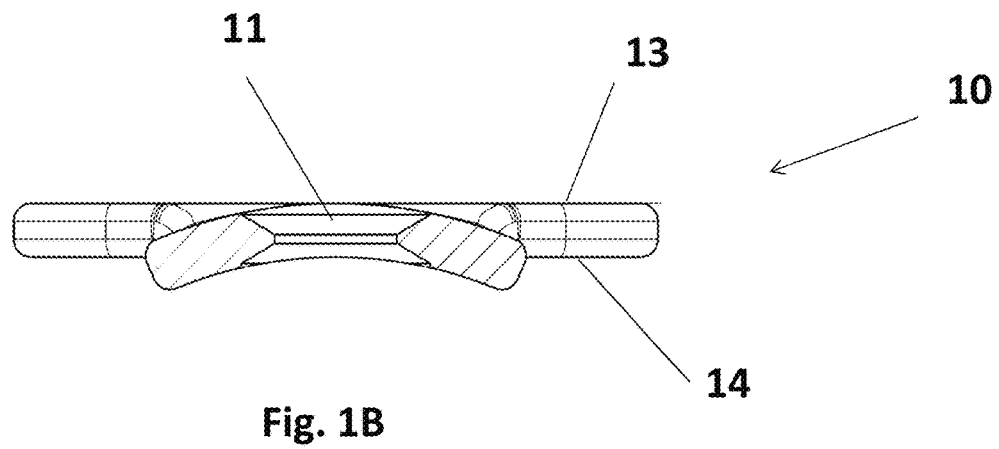
FIG. 1B is a cross-sectional view of FIG. 1A at cross-sectional line A-A.
Figure 1C:
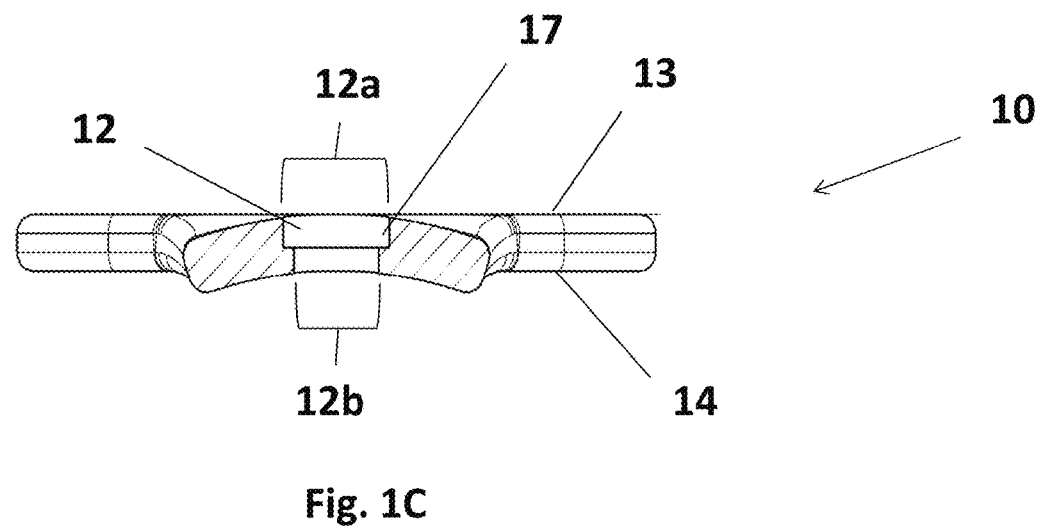
FIG. 1C is a cross-sectional view of FIG. 1A at cross-sectional line B-B.
Figure 1D:
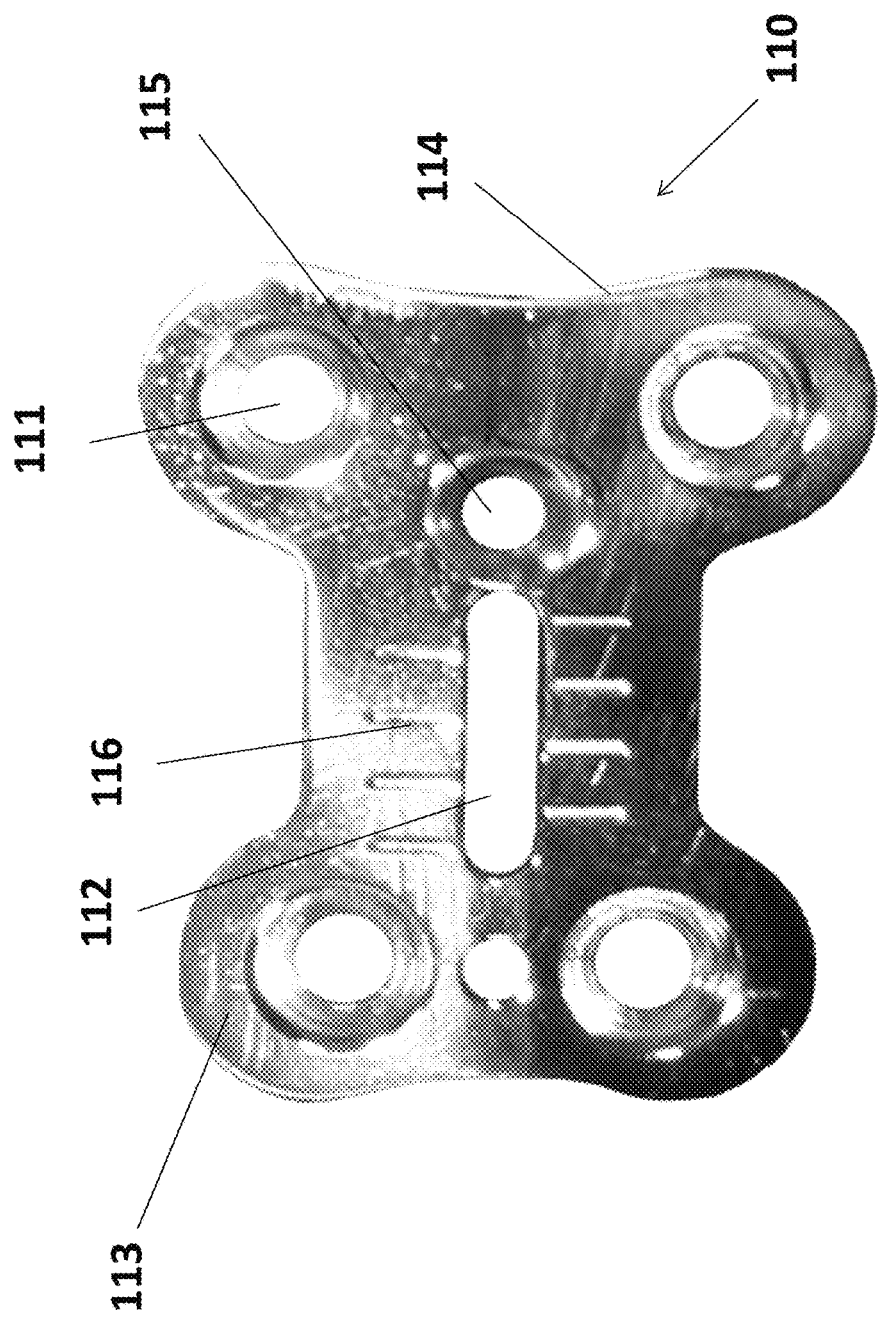
FIG. 1D is a top view of an alternative exemplary bone plate of the present invention.

An exemplary bone plate 10 is depicted in FIG. 1A, which shows a perspective view of one embodiment of the present invention. As shown, bone plate 10 has been configured for use with an implant or wedge implant 20 having a bone plate engagement portion comprising of, for example, a head 21 with a stem 22. Bone plate 10 preferably includes a plurality of holes and at least one track 12, each of which are openings extending from a top face 13 of plate 10 through to a bone-contacting face 14 of plate 10 (FIGS. 1B-C). Each hole 11 is preferably sized and shaped to accommodate a variety of screw types and sizes. For example, the interior surface of each hole 11 may include a tapered internal configuration that allows for the insertion of a fixation element, such as a compression or a locking screw. Each hole 11 may also be sized and tapered to permit the angulated insertion of one or more K-wires. In the design shown, some holes 11 employ a technology often referred to as the SmartLock Technology in several products offered by Stryker Trauma GmbH and Howmedica Osteonics Corp. In such a configuration, the interior surface is constructed of a softer material than a corresponding bone screw head so that insertion of the screw results in deformation of at least a portion of the interior of the screw hole. Other configurations for holes 11 are also contemplated, including threaded interior surfaces and the like. Plate 10 also has one or more conical holes 15. Each hole has interior surface that is tapered toward the bone-contacting face 14 of the plate 10 to facilitate the angled insertion of the K-wire through the top face 13, as shown in FIG. 1F with reference to a bone plate 210.

Figure 2A:
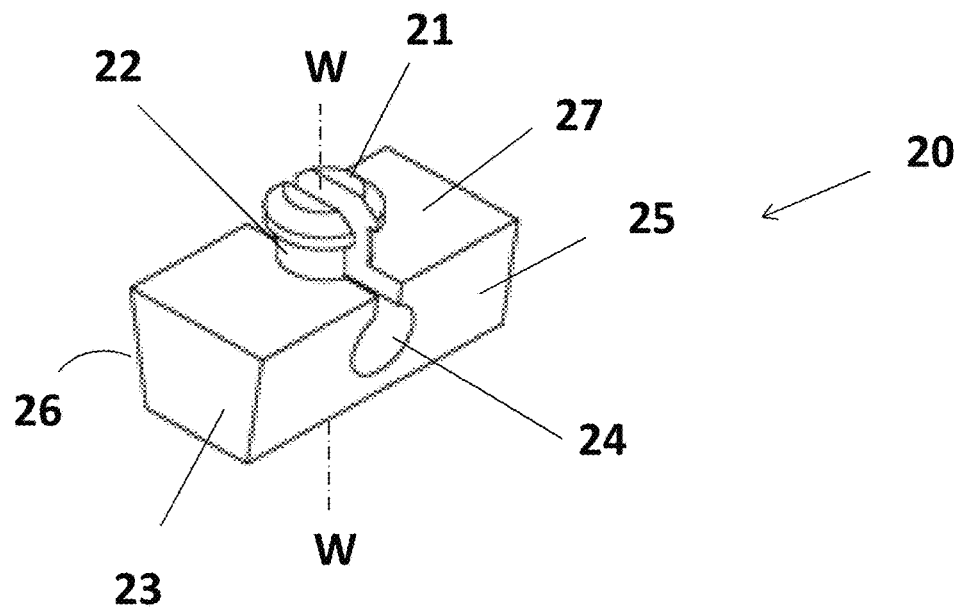
FIG. 2A is a perspective view of an exemplary wedge implant of the present invention.
Figure 2B:
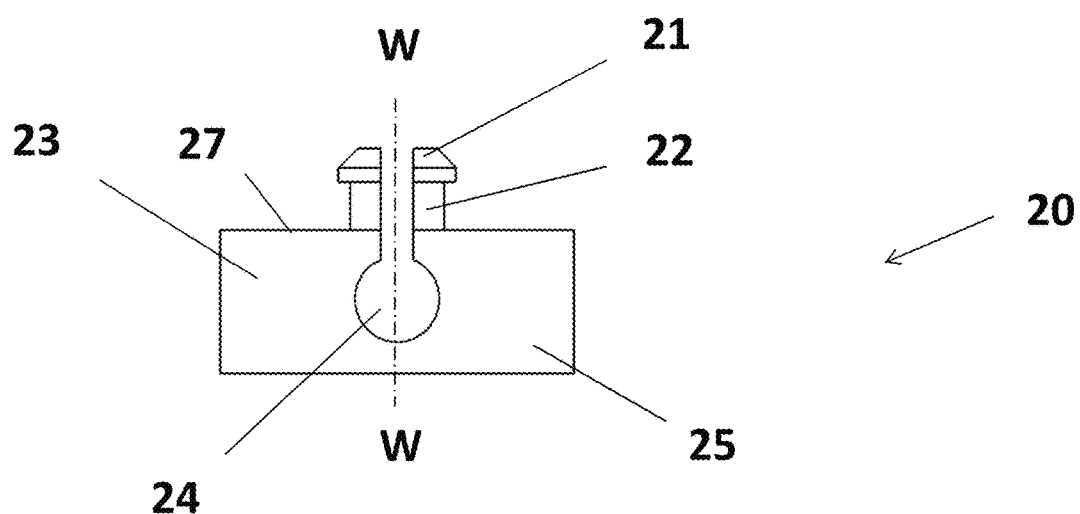
FIG. 2B is a front view of the wedge implant of FIG. 2A, the other side being a mirror image thereof.

In FIG. 1A, and the corresponding cross-section of FIG. 1C, track 12 of plate 10 is depicted as an elongated slot having two or more widths. In FIG. 1C, an outer or first width 12a is defined by the track 12 along the top face 13 of the plate 10. Track 12 steps or tapers towards an inner or second width 12b, which is defined by the track 12 along the bone-contacting face of plate 10. The inner width 12b may be wide enough to accommodate the stem 22 of wedge implant 20, whereas the outer width 12a may be wide enough to accommodate the head 21 of implant 20 (FIGS. 2A-2B). If track 12 steps towards the inner width, then a ledge surface 17 is formed to accommodate head 21 (FIG. 1C). Although shown as a straight, it is envisioned that the track 12 and ledge surface 17 could be any shape, including curved, round, or even substantially circular. Likewise, as in the alternative bone plate 110 of FIG. 1D, bone plate 10 could embody a number of different shapes, as well as feature different locations and configurations for each screw hole 11, conical hole 15, and track 12. For example, the shape of any embodiment of plate 10 and the relative locations of each hole 11 or 15, track 12, or ledge surface 17 may be modified to accommodate specific parts of the body, varying patient anatomies, or differing levels of deformity. Portions of any embodiment of bone plate 10 may be furnished in a variety of biocompatible materials, including titanium, stainless steel, polymers, bioresorbable polymers, magnesium foam, and the like.

Figure 2C:
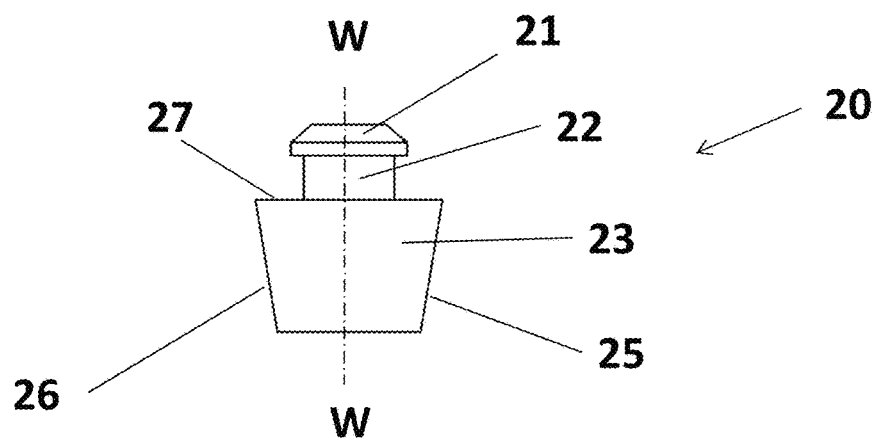
FIG. 2C is a side view of the wedge implant of FIG. 2A, the other side being a mirror image thereof.

FIGS. 2A-2C show, respectively, perspective, front, and side views of one embodiment of wedge implant 20. As shown, implant 20 has an engagement portion that is adapted to pass through the track 12 so as to movably engage implant 20 with the bone plate 10. The illustrated engagement portion comprises at least the head 21 and the stem 22. In FIGS. 2A-C, head 21 is be connected to stem 22 and body 23 along a longitudinal wedge axis W-W of implant 20. A top surface 27 of wedge body 23 may be shaped to correspond with a portion of the bone contacting face 14 of bone plate 10. For example, top surface 27 in FIGS. 2A-C is a flat surface corresponding to a generally flat bone-contacting surface 14 of one embodiment of plate 10. Another example is provided with respect to wedge implant 120 in FIG. 2D, wherein a top surface 127 of a wedge body 123 is curved to correspond with a curved bone contacting surface 14 of another embodiment of bone plate 10 (FIG. 1D).

Figure 2D:
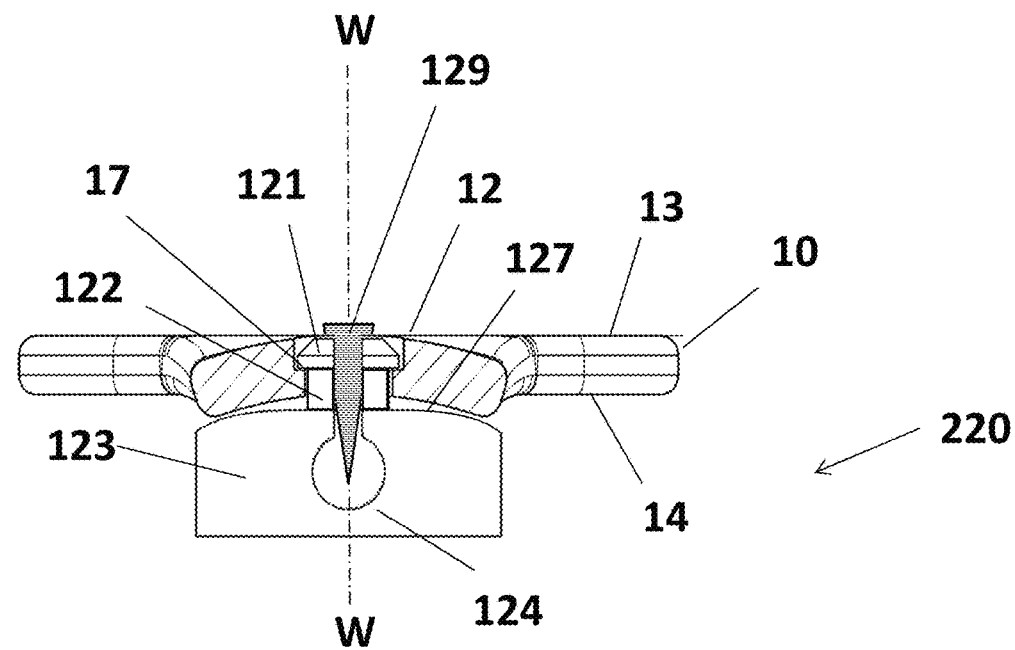
FIG. 2D is a front view of another exemplary wedge implant 10 engaged with a bone plate and a locking element.

The engagement portion described herein preferably allows any embodiment of wedge implant 20 to be movably engaged with an embodiment of bone plate 10. Stem 22, for example, is preferably sized to slide and rotate within the inner width 12b of track 12. The cross-sectional width of the head 21 in FIGS. 2A-E is preferably larger than the inner width 12b of track 12, but smaller than the outer width 12a of track 12. Thus, the head 21 is preferably sized to slide and rotate within the outer width 12a. Because of this configuration, wedge implant 20 may be anchored in track 12, adapted to move relative to ledge surface 17, and yet prevented from disengaging from plate 10, without further attachment means, by allowing head 21 to pass back through the inner width 12b of the track 12. As shown in FIG. 2D, the top of head 121, for example, may be sized to fit flush within the track 12, i.e., without protruding past the top face 13 of plate 10, thereby leaving the top face 13 of plate 10 to define its top-most profile.

Figure 2E:
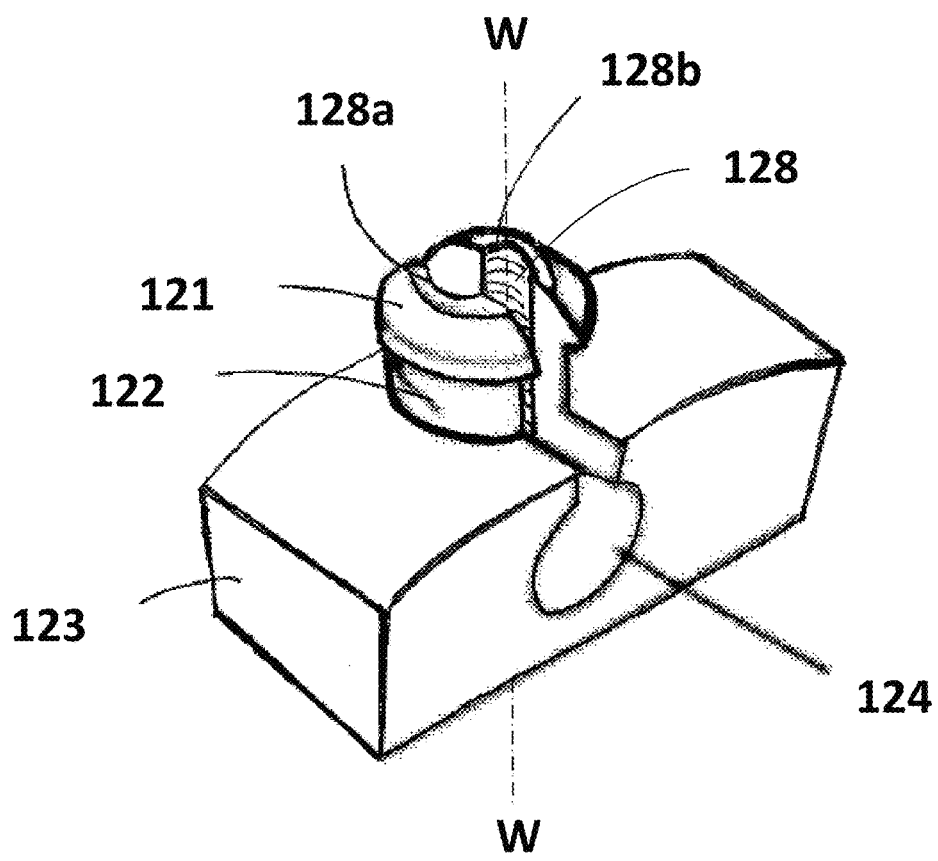
FIG. 2E is a perspective view of the wedge implant of FIG. 2D without the bone plate.
Figure 3A:
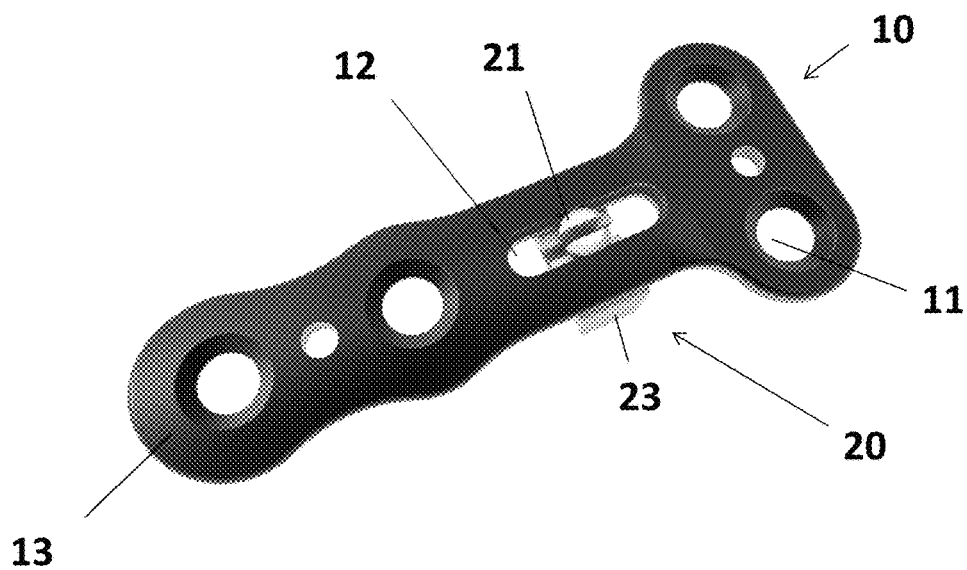
FIG. 3A is a top perspective view of the wedge implant of FIG. 2A engaged with the bone plate of FIG. 1A.
Figure 3B:
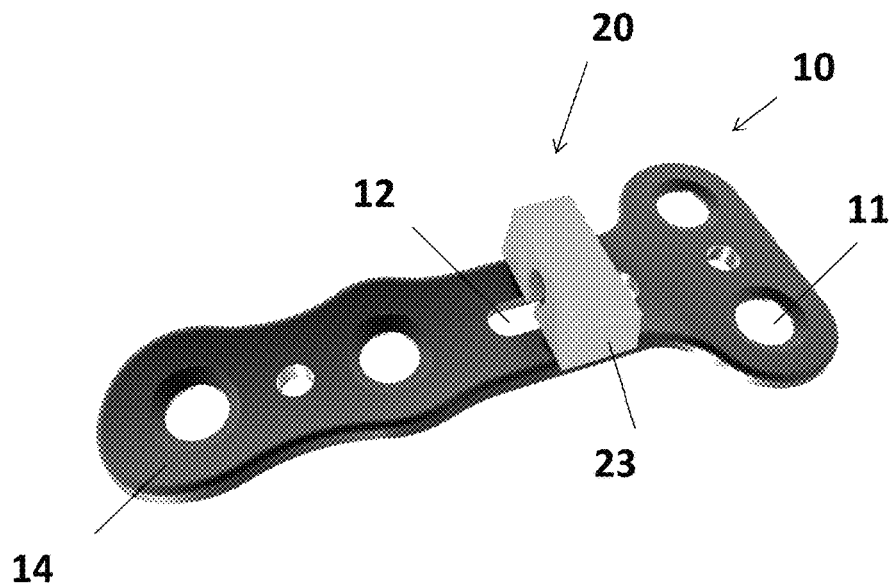
FIG. 3B is a bottom perspective view of the construct of FIG. 3A.

The engagement portion of wedge implant 20 also allows portions of implant 20 to move, as needed, to engage bone plate 10. Elements of implant 20 may deform to facilitate said movements. In the embodiment of implant 20 shown in FIGS. 2A-C, for example, an aperture 24 extends from a front face 25 of wedge body 23 through to a rear face 26 of body 23 such that at least the head 21 and stem 22 are divided into first and second engagement portions. Body 23 may also be partially divided. Aperture 24 thereby facilitates the deformation of wedge implant 20 by creating a living hinge in body 23 that allows the first and second engagement portions to move toward one another while passing through track 12 of the plate 10 (FIGS. 3A-B). Preferably, the deformation of the head 21 and stem 22 is elastic, such that implant 20 returns to its original shape after each engagement portion is passed through track 12. For example, each divided portion of head 21 and stem 22 in the embodiments illustrated in FIGS. 2A-E may be formed integrally with wedge body 23 such that body 23 is held within the track 12 by stem 22 and anchored to the track 12 by head 21. The exterior surface of each engagement portion is preferably biased against an interior surface of track 12 by the living hinge. Advantageously, this configuration also allows wedge 20 to be movably engaged in track 12 without the use of further attachment elements, such as screws and the like. In some embodiments, the engagement portion is passed through the track 12 so as to slidably and rotatably engage the wedge body 23 with the bone plate 10.

Many elements of bone plate 10 and wedge implant 20 can be varied without departing from the present invention. A number of alternatives are now described. Some of these varied elements are described herein with reference to a plate 10, 110, etc., or a wedge 20, 120, etc., although any plate may be used with any implant. Related and kits and methods are also described with reference these varied embodiments of plate 10 and implant 20. Of course, any feature of any element described in reference to any alternative embodiment may also be incorporated into any other embodiment of the present invention.

One alternative embodiment of bone plate 110, shown for example in FIG. 1D, preferably includes at least one screw hole 111 disposed on each end of the plate 110. Each hole 111 is preferably adapted to receive a screw 40 (e.g., FIGS. 4A-B). Plate 110 may also have at least one cylindrical or conical hole 115 disposed on each end of the plate 110. Each hole 115 is preferably adapted to receive a K-wire. The interior surfaces of conical hole 115 may be tapered toward the bone-contacting face 114 of the plate 110 to facilitate the angled insertion of the K-wire through the top face 113, as shown in FIG. 1F with respect to plate 210. A plurality of hatch marks 116 may be disposed along the length of track 112 to assist a user in measuring the size of an osteotomy gap (FIGS. 4A-B) over which the plate 110 is to be secured. Marks 116 may be spaced apart or arranged at regular intervals to aid in the selection of the appropriate wedge implant 120 for filling the osteotomy gap 31. For example, marks 116 may indicate the desired size of implant 20 when a portion of body 23 is aligned with one of the marks 116. Depending on the furnished material, marks 116 may be formed on or etched into plate 110.

Figure 1E:
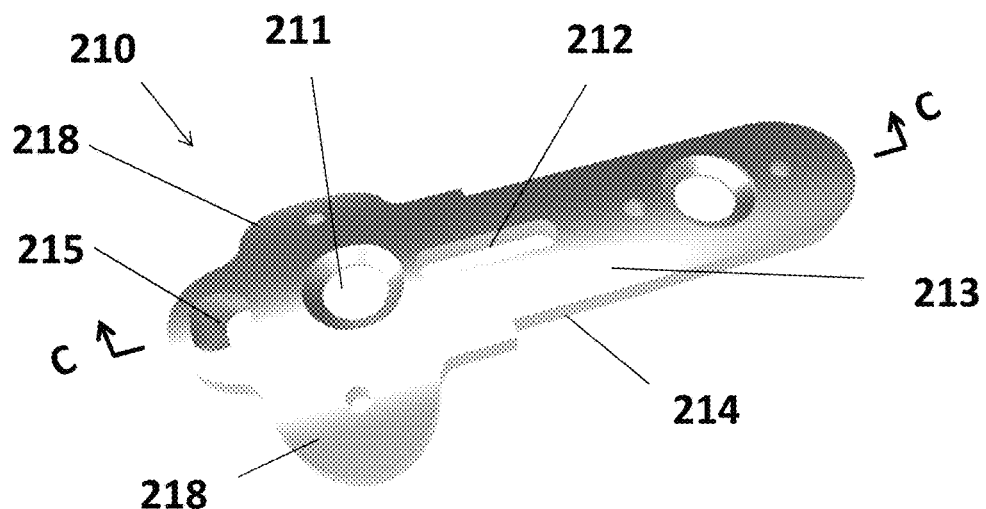
FIG. 1E is a perspective view of another alternative exemplary bone plate of the present invention.
Figure 1F:
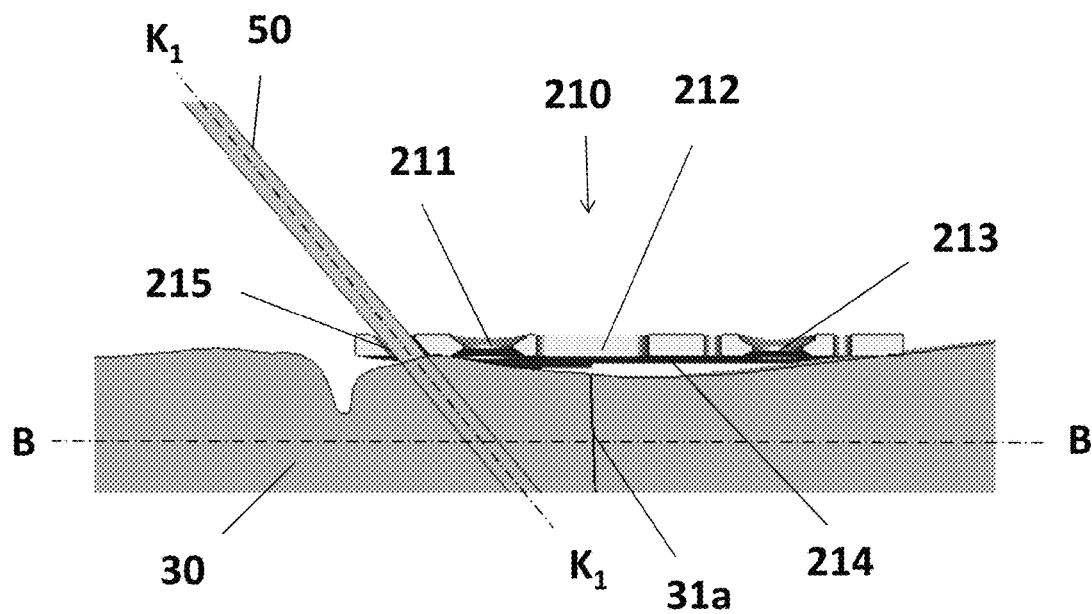
FIG. 1F is a section view of the bone plate of FIG. 1E at cross-sectional line C-C after the plate has been placed on a bone and a K-wire has been inserted therethrough.

Another alternative bone plate 210 is depicted in FIGS. 1E-F. Bone plate 210 may be embodied as a non-implanted template or an implantable bone plate, like plates 10 and 110. As shown, plate 210 has a track 212, a plurality of holes 211, and at least one conical hole 215. Although not required, plate 210 has a pair of wings 218 that extend out from each side of plate 210. Each wing 218 is curved to surround a portion of bone 30. A hole 211 is provided on each wing 218. As noted above, conical hole 215 of plate 210 is adapted to receive a K-wire 50. For example, in FIG. 1F, hole 215 is illustrated has having an interior surface that is tapered toward the bone-contacting face 214 of the plate 210 to facilitate the angled insertion of K-wire 50 through the top face 213. The tapering of conical hole 215 relative to hole 211 and track 212 allows K-wire 50 has been inserted through hole 215 and bone 30 along an insertion axis K-K that is oblique to a longitudinal axis B-B of bone 30 (FIG. 1F).

Components of each embodiment of bone plate 10 may also be modified. Track 12 of FIG. 2D, for example, may have a deformable portion. Much like hole 11, the interior surface of track 12 may be constructed of a softer material. For example, locking element 129 may be inserted between the divided portions of head 121 and stem 122 to fix the position of wedge implant 120 relative to plate 10. Element 129 in FIG. 1D is a conical screw with a continuously increasing diameter along axis W-W. Ledge 17 may be formed of a softer material than the conical screw so that the position of implant 120 is fixed when ledge 17 deforms to receive the screw. For example, element 129 may be screwed into the divided portions of head 121 and stem 122 until ledge 17 is at least partially deformed to prevent implant 120 from moving in track 12 relative to bone plate 10. One example of such a construction is included in various SmartLock® products offered by Howmedica Osteonics Corp.

Alternative embodiments of wedge implant 20 are now described. For example, aperture 24 is shown in FIGS. 2A-E as a single cut that divides head 21 and stem 22 into two halves. It is envisioned that the aperture 24 could vary in shape, orientation, or even the number of apertures 24 provided. Although shown has having two divided portions, wedge implant 20 may have multiple cuts through the head 21 and stem 22 to provide multiple apertures 24 through the wedge body 23, thereby dividing head 21 and stem 22 into multiple divided portions. The additional deformability provided by varying aperture 24 may permit certain movements of bone plate 10 relative to wedge body 23, such as twisting movements and the like; or allow for bone plate 10 to be more easily detached from the wedge implant 20. Either of these alternatives may be necessary, for example, in cases where a patient experiences problems with the plate 10 after implantation.

To further facilitate its insertion into the track 12 along axis W-W, head 21 may be stepped or tapered away from the wedge body 23 in a direction towards axis W-W, much like the trapezoidal prism illustrated in FIGS. 2A-C. Likewise, the cross-section of head 21 and stem 22 may be of any shape suitable for moveable reception within the track 12. For instance, instead of being generally circular, such elements could be square. Any portion of wedge implant 20 may be furnished in a variety of biocompatible different materials, including titanium, stainless steel, polymers, bioresorbable polymers, magnesium foam, and the like. The materials may promote bone growth or healing, or allow bone growth within the implant 20. Additionally, at least a portion of the wedge implant 20 may be furnished in a different material than the rest of the implant 20 in order to facilitate its insertion into the track 12, as discussed further below.

FIGS. 3A and 3B show top and bottom perspective views, respectively, of a plate 10 engaged with a wedge 20. As shown, the head 21 is situated through track 12 such that wedge 20 is held in track 12. Track 12 is illustrated as being securely located between the head 21 and wedge body 23. This configuration preferably enables wedge 20 to rotate about or slide along the track 12, thereby permitting a range of orientations by which the plate 10 may be secured to a bone while engaged with the wedge 20. It is to be understood that the head 21 and stem 22 of wedge implant 20 may be adapted to slidably and rotatably engage track in a variety of alternative configurations, each defining a means for moveably engaging wedge implant 20 with track 12.

Figure 3C:
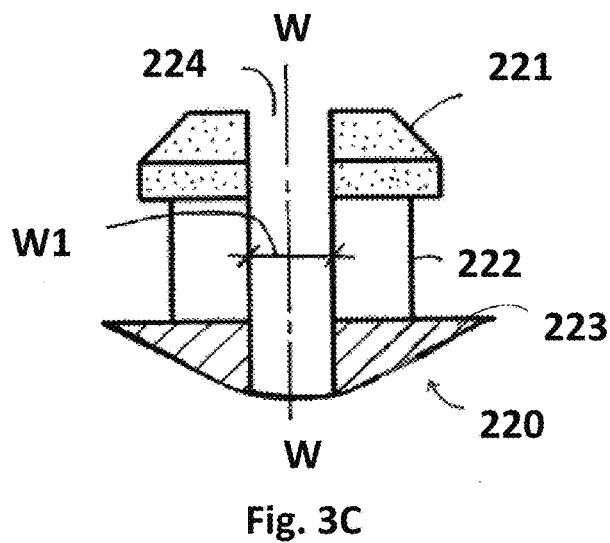
FIG. 3C is a side view of an exemplary embodiment of an engagement portion of a wedge implant in accordance with the present invention.

As shown in FIG. 3C, for example, an alternative head 221 may be adapted to snap into track 12. In this embodiment, the material composition of wedge 220 and the shape of an aperture 224 resiliently biases each divided part of head 221 and stem 222 apart from one another. The resulting biasing force may allow the divided parts of at least stem 222, for example, to maintain a pre-determined spatial relationship, shown in FIG. 3C as a measurement W1. Preferably, this biasing force compels each divided part of head 221 and stem 222 to snap back to dimension W1 after being compressed together during engagement with track 12, or any time thereafter, to ensure that head 221 remains slidable within track 12. Wedge 220 may advantageously be composed entirely of the same resilient material, wherein the undivided portions of wedge body 223 act as a living hinge. Preferably, the resilient biasing force of the material combined with force enhancing shape of aperture 224 sufficiently secures wedge 220 within bone plate 10.

Although not required to engage wedge implant 20 with plate 10, each divided part of head 21 and stem 22 might be alternatively adapted to receive an elongated object between their respective divided portions. The elongated object may be a K-wire for positioning wedge body 23. Alternatively, the object may be an element for fixing the position of wedge 20 relative to bone plate 10. For example, a locking element, like a screw, might be inserted between the divided portions of head 21 and stem 22 along wedge axis W-W to fix the position of wedge 20 with respect to plate 10 by pinning the sides of at least stem 122 against an interior surface of track 12, such as ledge 17.

An exemplary locking element 129 is depicted in FIG. 2D with reference the engagement portion of wedge implant 120, which comprises head 121 and stem 122. Locking element 129 is depicted as a conical screw that is preferably inserted between the divided portions of head 121 and stem 122 to fix the position of wedge implant 120 in track 12. The internal surfaces of head 121, stem 122, and aperture 124 may be further adapted to receive the locking element 129. For example, a threaded hole may be placed in aperture 124 to receive a corresponding set of threads on locking element 129. Alternatively, each internal surface of the divided portions of head 121 and stem 122 may be threaded to receive the threads on locking element 129. As shown in FIG. 2E, for example, each of said interior surfaces may also have a semi-circular portion 128a that defines a split bore 128 between head 121 and stem 122. Any portion of said interior surfaces, such as either of the semi-circular portions 128a, may be threaded, tapered, or likewise formed to receive element 129. In some embodiments, a portion of said interior surfaces may be formed of a softer material than locking element 129, similar to holes 11 and 15 described above, so as to deform when receiving element 129 there between. Upon insertion of element 129, the divided portions of head 121 and stem 122 can be prevented from moving toward, or even away from one another.

Figure 3D:
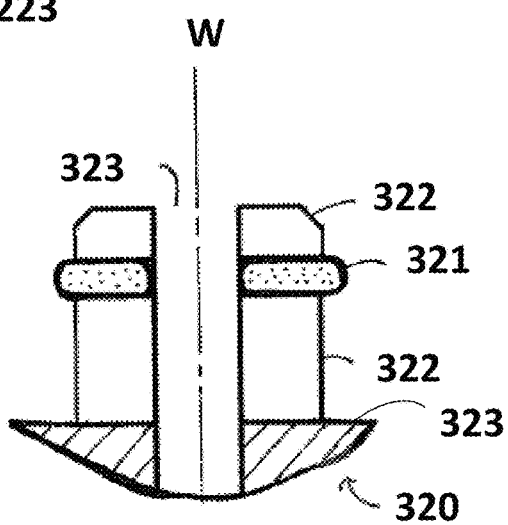
FIG. 3D is a side view of an alternate embodiment of the engagement portion of FIG. 3C.
Figure 3E:
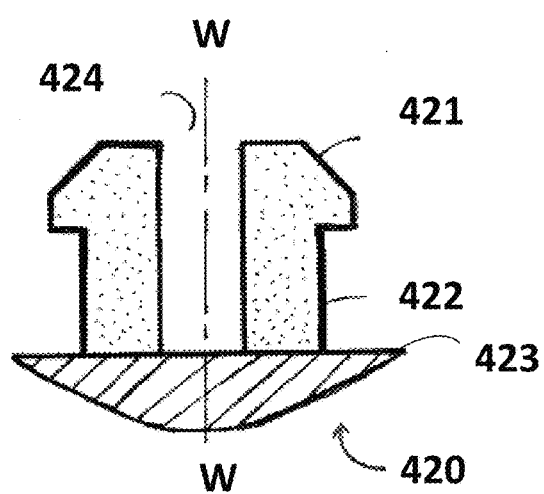
FIG. 3E is a side view of another alternate embodiment of the engagement portion of FIG. 3D.

Alternatively, another embodiment of head 21 and stem 22 may be adapted to deform into track 12, independent of wedge body 23, because at least a portion of either element is composed of an elastically deformable material. Variants are shown in FIGS. 3C-E, wherein the dotted elements may be composed of an elastically deformable material. As shown particularly in FIG. 3C, head 221 may be composed of an elastically deformable material while stem 222 is not. For example, head 221 may be a sleeve-like or annular element that is attachable to an open end of stem 222. Said open end may have a reduced diameter and/or a locking portion adapted to receive of head 221 such that the flanges of head 221 may deform outwardly into track 12 when engaged therewith, after being passed therethrough. Alternatively still, a head 321 of FIG. 3D is ring-like or torus element and, thus, capturable within a correspondingly shaped groove (not shown) on a stem 322. Head 321 may be sized to compress against stem 322 in the groove, thereby permitting head 321 to deform while passing through the track and then, preferably, rebound onto ledge surface 17 without being removed from the groove 12. As shown in FIG. 3E, the entirety of both a head 421 and a stem 422 may alternatively be composed of an elastically deformable material, while body 423 is not. Advantageously, this embodiment permits head 421 and stem 422 to be engaged with track 12 even if aperture 424 does not extend into a portion of wedge body 423. Moreover, it also allows each of head 421 and stem 422 to be readily constructed from a first material, such as a metallic material adapted to engage track 12; and attached to a body 423 constructed from a second material, such as a polymer.

If some portions of head 21 and stem 22 are deformable, then locking element 129 (FIG. 2D) may also be inserted between or screwed into the deformable portions of those elements to further secure wedge 20 to plate 10. For example, an embodiment of element 129 may be inserted between the divided portions of head 221 and stem 222 after head 222 has been deformed to place head 221 in track 12. Inserting element 129 may fix the position of wedge 220 (or wedge 20, 120, 320, or 420) with respect to plate 10 by pinning certain exterior surfaces of head 221 and stem 222 against the interior surfaces of track 12. For the embodiment of FIG. 3C, locking element 129 would be utilized to pin the divided portions of at least stem 222 against the interior surfaces of track 12, such as ledge 17. If a portion of implant 20 is undivided, as in FIG. 3E, then element 129 may alternatively be screwed into a deformable core of any embodiment of head 421 and stem 422 and/or wedge body 423 so as to fix the position of wedge 20 by increasing the diameter of stem 422.

Any embodiment of head 21 and stem 22 may alternatively assume a T-shaped profile (e.g., FIG. 3E) with a rectangular cross-section (not shown) having a width less than the width of track 12. An alternate embodiment of head 421 and stem 422 of FIG. 3E, for example, may be inserted through track 12 and rotated about axis W-W until each flange of the T-shaped profile engages a portion of track 12, such as the interior surfaces of track 12 or ledge surface 17. Each divided part of head 421 and stem 422 may be resiliently biased away from axis W-W to further secure wedge 420 in track 12. Preferably, the T-shaped head 421 and stem 421 are rotatably engaged with track 12 after being rotated approximately ninety degrees about axis W-W. Of course, some embodiments of T-shaped head 421 and stem 422 may be received within track 12 in the absence of a resilient biasing force, much like a key and lock. Some embodiments of track 12 may, for example, may permit the use of a narrowed wedge implant 420. Narrowed wedge 420 may have an alternate wedge body 423 with a rectangular profile that is adapted to pass directly through track 12 and into osteotomy gap 31 when either slid along or attached to K-wire 50 (e.g., FIG. 4E). An embodiment of locking element 129 may, as above, be inserted between the divided portions of any T-shaped embodiment of wedge implant 420 to fix its position relative to bone plate 10.

Much like head 21 and track 22, numerous alternative embodiments of wedge body 23 are also contemplated. Each of these alternative embodiments is described with reference to FIGS. 2A-E. For example, although shown as a trapezoidal prism, wedge body may resemble a variety of shapes and sizes, regular or irregular, to correspond with the shape of bone removed in any osteotomy procedure. Some methods described below, for example, may be used with an implant 20 having a body 23 of any size or shape. In a further example, the wedge 20 of FIG. 2B may have a bore extending through the entirety of wedge body 23 along wedge axis W-W. The bore may be adapted to slidably receive an elongated object, such as K-wire 50 or locking element 129, therethrough. Wedge implant 20 may alternatively have a bore that terminates within a capture portion of wedge body 23. Preferably, this capture portion is adapted to engage an end of K-wire 50 (not shown). This permits bone plate 10 to be slid along K-wire 50 and positioned proximate to wedge 20. Alternatively still, if K-wire 50 is a rigid or semi-rigid element, then this configuration may also permit the use of K-wire 50 as a means to place or slide wedge 20 into osteotomy gap 31.

Although depicted as a smooth surface in FIG. 2A, for example, either the first or second face 25, 26 of wedge body 23 may be adapted for frictional engagement with a bone surface so as to help to secure wedge 20 within gap 31. For example, either surface could be intentionally roughed. Alternatively, either the first or second face 25, 26 of wedge body 23 may be adapted to slide along a bone surface in a first direction and frictional engage the same surface when slid in a second direction opposite of the first direction. For example, at least first face 25 of body 23 might have pattern of grooves and cuts, such as siping, that is adapted for one-way deflection when placed against the first or second faces 32 and 33 of gap 31 (FIG. 4A) so as to prevent wedge body 23 from retreating out of osteotomy gap 31. Wedge body 23 in FIG. 2A, for example, is depicted as solid portion of wedge 20. Alternatively, wedge body 23 may have an interior void defined by the removal of any structural unnecessary material. The remaining exterior shell of wedge body 23 may form a set of integrally formed beams, columns, and plates adapted to maintain gap 31 (FIGS. 4A-B) in a particular position, at least during implantation or until a subsequent point of fusion with bone 30. The interior void may be in communication with the bore extending fully or partially through body 23 so as to permit insertion of healing materials into the void through the bore. In some embodiments, an elongated element with a cannula may be inserted into the bore so as to both fix the position of wedge 20 relative to plate 10 and permit insertion of healing materials into the void through the cannula.

Figure 4A:
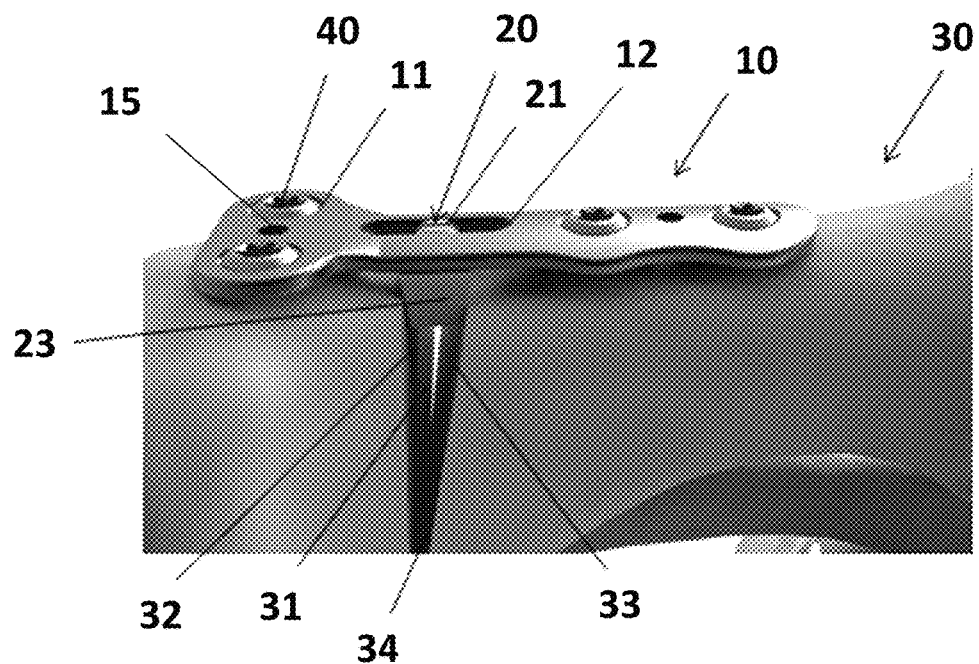
FIG. 4A is a side view of the construct of FIG. 3A secured to a prosthetic bone.
Figure 4B:
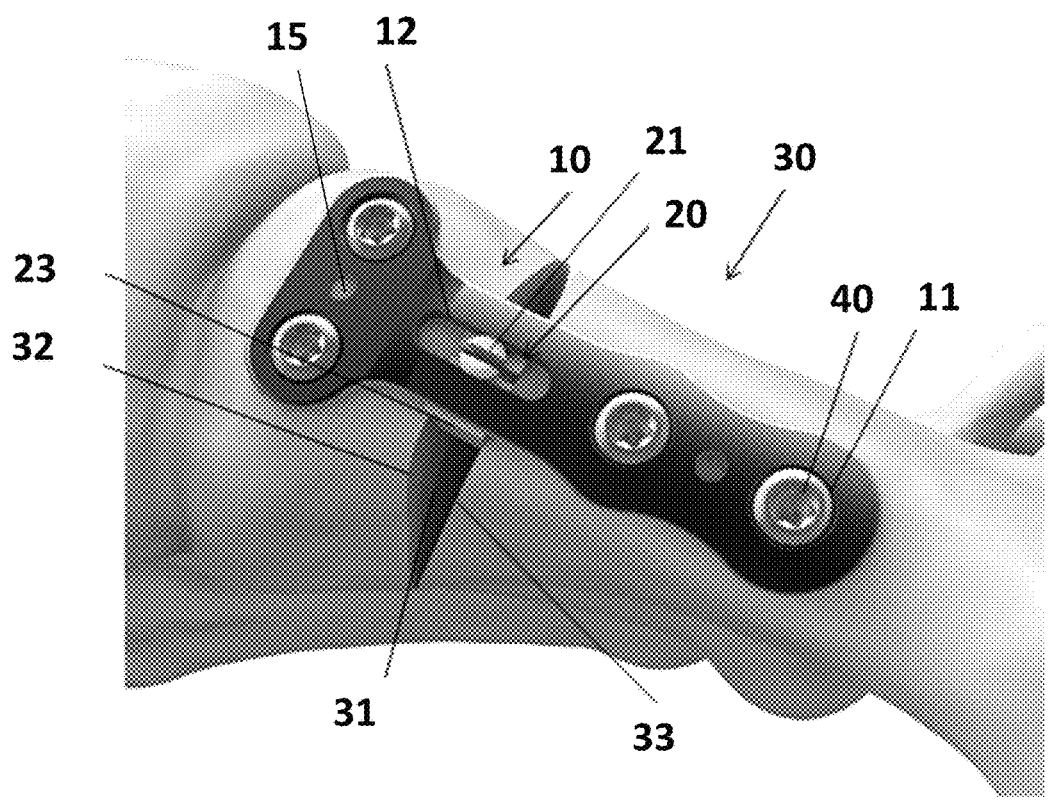
FIG. 4B is a top perspective view of the construct and prosthetic bone of FIG. 4A.

Alternatively, either the first or second faces 25 or 26 of wedge body 423 may have a cut-out in communication with the interior void so that any healing materials placed in the void may be in immediate contact with both wedge body 23 and the faces 32, 33 of gap 31 (FIG. 4A). For example, the healing material could be a bone cement adapted to flow through the bore to fill the interior void, thereby allowing wedge body 23 to be fused in gap 31 without having to pump any excess healing material into the body. Alternatively still, the cut-out may comprise a perforated surface, filtering element, or like structure that permits the healing material to flow therethrough in particular manner or direction within gap 31. In either embodiment, the remaining exterior shell of wedge member 20 may serve to maintain gap 31 while acting as a distribution nozzle for the healing material, wherein the healing material preferably flows into the interior void through the bore. For example, the healing material may flow into the bore from a cannula within K-wire 50 or other cannulated delivery device, such as an embodiment of locking element 129 having a cannula extending therethrough.

Figure 4C:
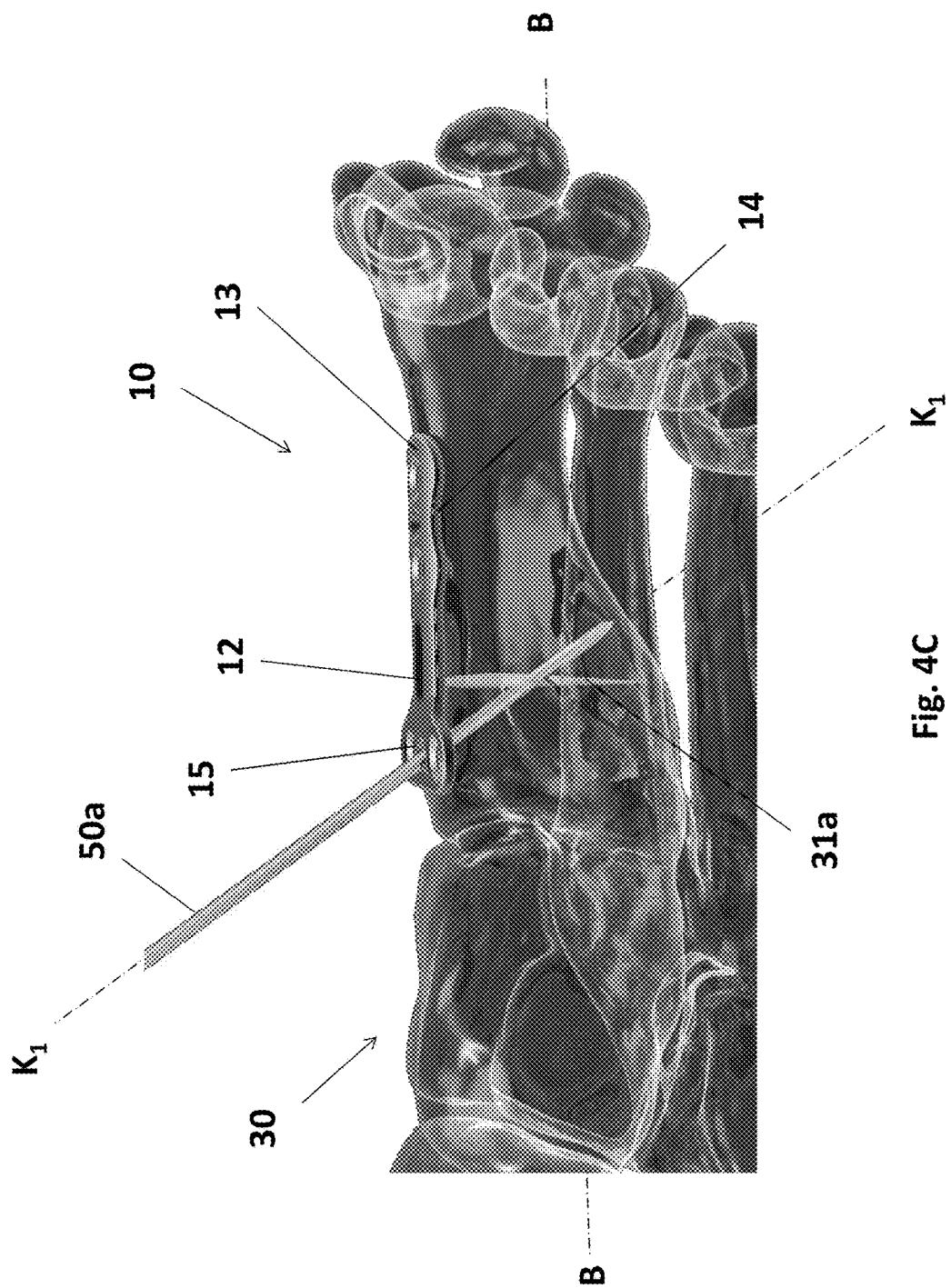
FIG. 4C is a side view of the bone plate of FIG. 1A after it has been placed on a transparent bone and a first K-wire has been inserted therethrough.
Figure 4D:
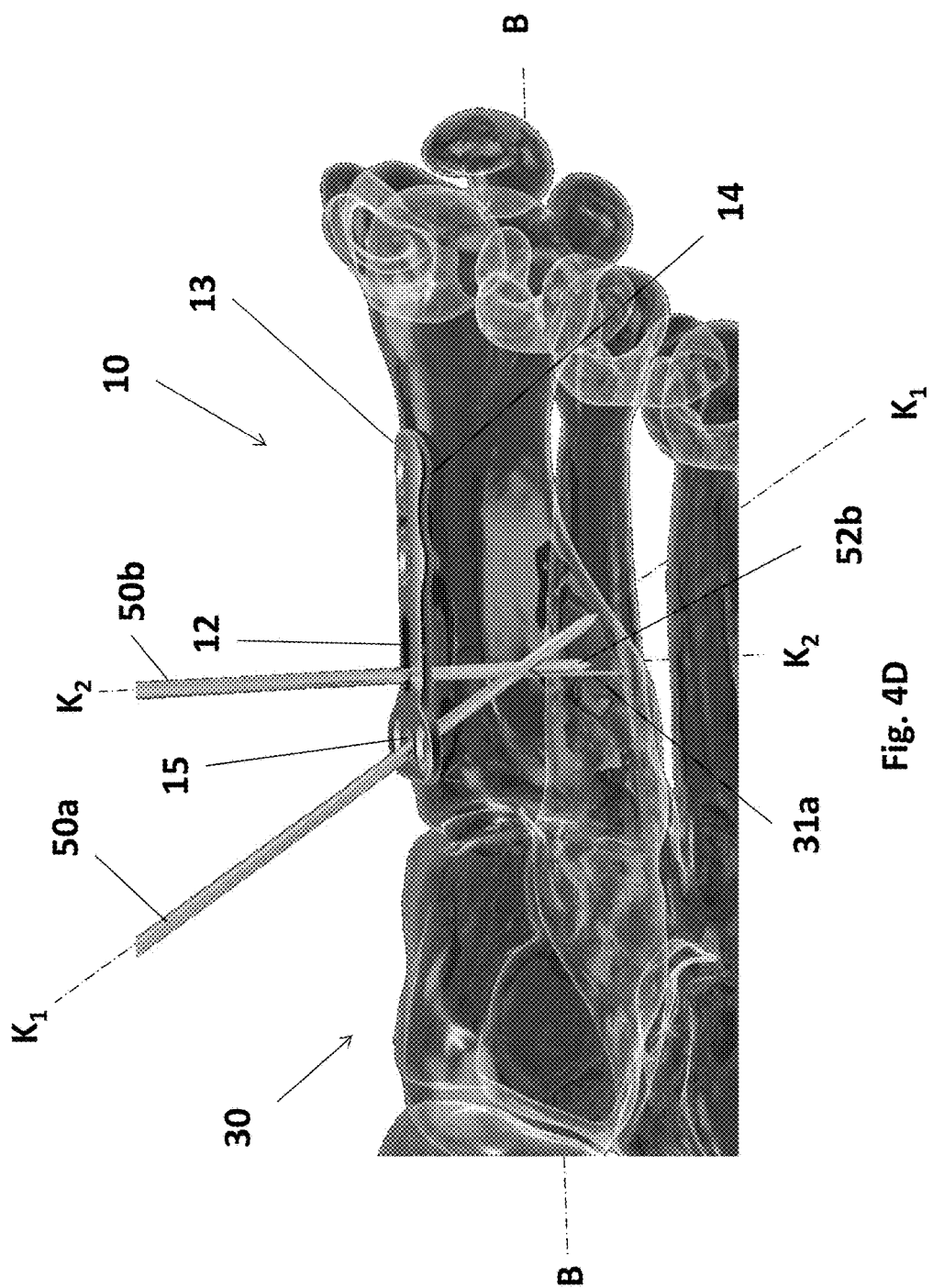
FIG. 4D is a side view of the plate of FIG. 4C after a second K-wire has been inserted therethrough.
Figure 4E:
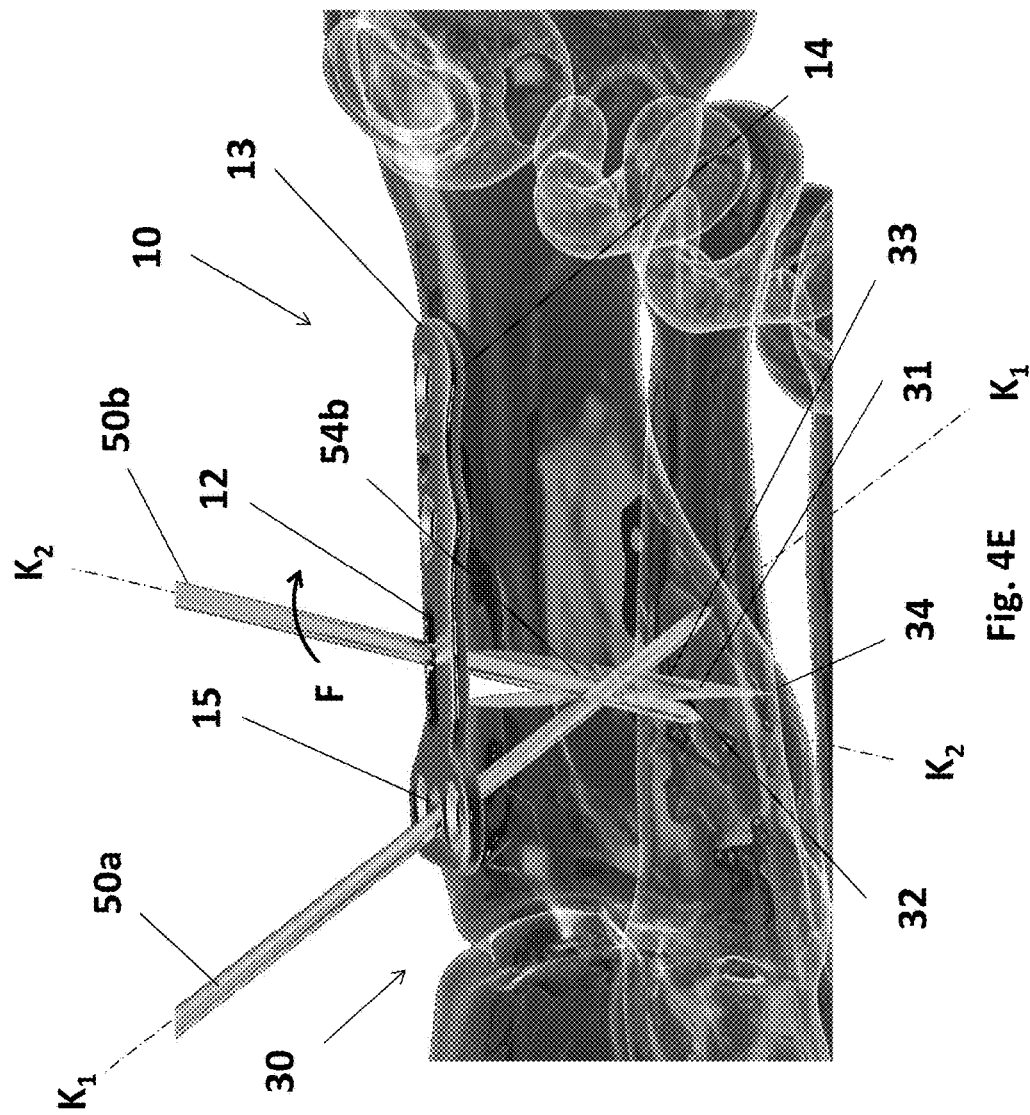
FIG. 4E is a side view of the plate of FIG. 4D after the first and second K-wires have been used to create a gap.

Numerous methods and kits are now described with reference to the various embodiments of bone plate 10 and wedge implant 20 described herein. An exemplary method of forming osteotomy gap 31 is illustrated in FIGS. 4C-E, wherein plate 10 has been placed against a bone 30 (shown transparent) so that track 12 of plate 10 may be used as a guiding template. This method first comprises performing a partial cut 31a on a portion of bone 20 and placing the bone-contacting face 14 of plate 10 adjacent the cut 31a. Preferably, as in FIG. 4C, a portion of track 12 is placed directly over partial cut 31a. A next step comprises inserting a first K-wire 50a into conical hole 15 along a first insertion axis $K_1$-$K_1$ that is oblique to the longitudinal axis B-B of the bone 30 (FIG. 4C). Preferably, insertion axis $K_1$-$K_1$ is substantially parallel to the interior surfaces of conical hole 15, as best shown in FIG. 1F with respect to hole 215.

First K-wire 50a is inserted into bone 30 until it spans across partial cut 31a (FIG. 4C). With first K-wire 50a in position, a second K-wire 50b is inserted into partial cut 31a through track 12 along a second insertion axis $K_2$-$K_2$ that is oblique with bone axis B-B yet substantially parallel to partial cut 31a (FIG. 4D). The first and second K-wires 50a and 50b may now be used as levers to produce an osteotomy gap 31. For example, the proximal tip 52b of K-wire 50b is driven into partial gap 31a to define a fulcrum point in bone 30. A next step comprises applying a force F to second K-wire 50b that spreads open cut 31a to form an osteotomy gap 31 with a first face 32, a second face 33, and a hinge 34 (FIG. 4E). Force F preferably pushes a contact surface 54b of K-wire 50b against bone 30 by rotating K-wire 50b about the fulcrum point until partial gap 31a is pried open to form osteotomy gap 31. Contact surface 54b of second K-wire 50b preferably remains parallel with second face 33 after gap 31 is formed.

In this method, track 12 guides second K-wire 50b in an intended direction to ensure that force F is properly applied. Track 12 also stabilizes K-wire 50b. For example, K-wire 50b may be an elongated metallic object with a small diameter that, in some procedures, might unintentionally deflect, bend, or buckle in response to force F without the guidance and support of track 12. These unintended movements may cause osteotomy gap 31 to form improperly or damage hinge 34. Track 12 reduces such risks by decreasing the unsupported length of K-wire 50b. To provide even greater support for track 12, bone plate 10 may be secured to bone 30 at any point during this method. For example, in some embodiments, one end of bone plate 10 is anchored to bone 30 by a screw 40 placed into one of the holes 11.

Figure 5A:
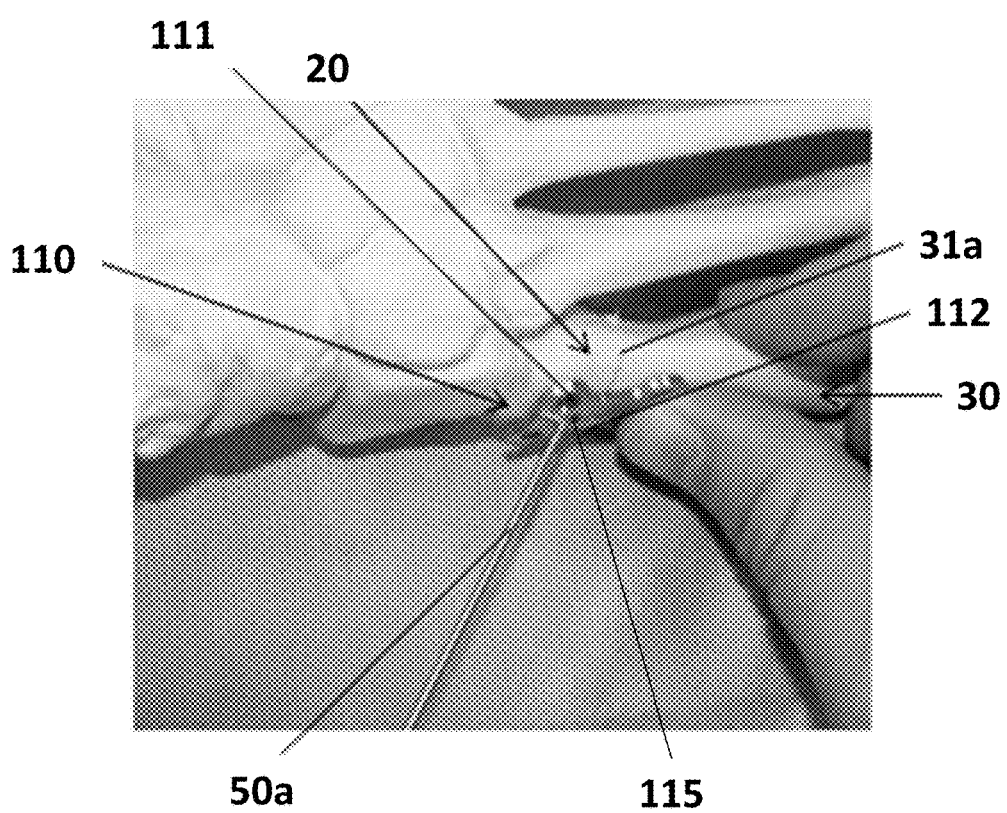
FIG. 5A is a perspective view of the bone plate of FIG. 1D after it has been placed on a bone and a first K-wire has been inserted therethrough.
Figure 5B:
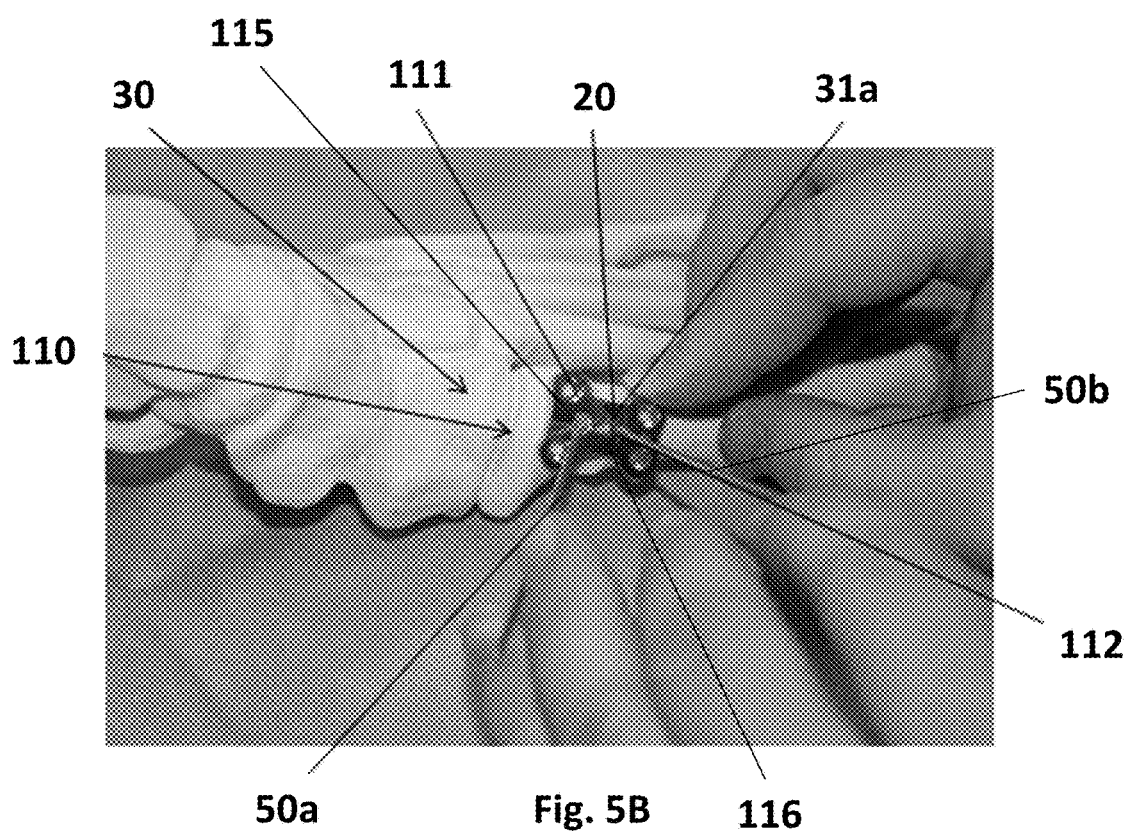
FIG. 5B is a side perspective view of the plate of FIG. 5A after a second K-wire has been inserted therethrough.
Figure 5C:
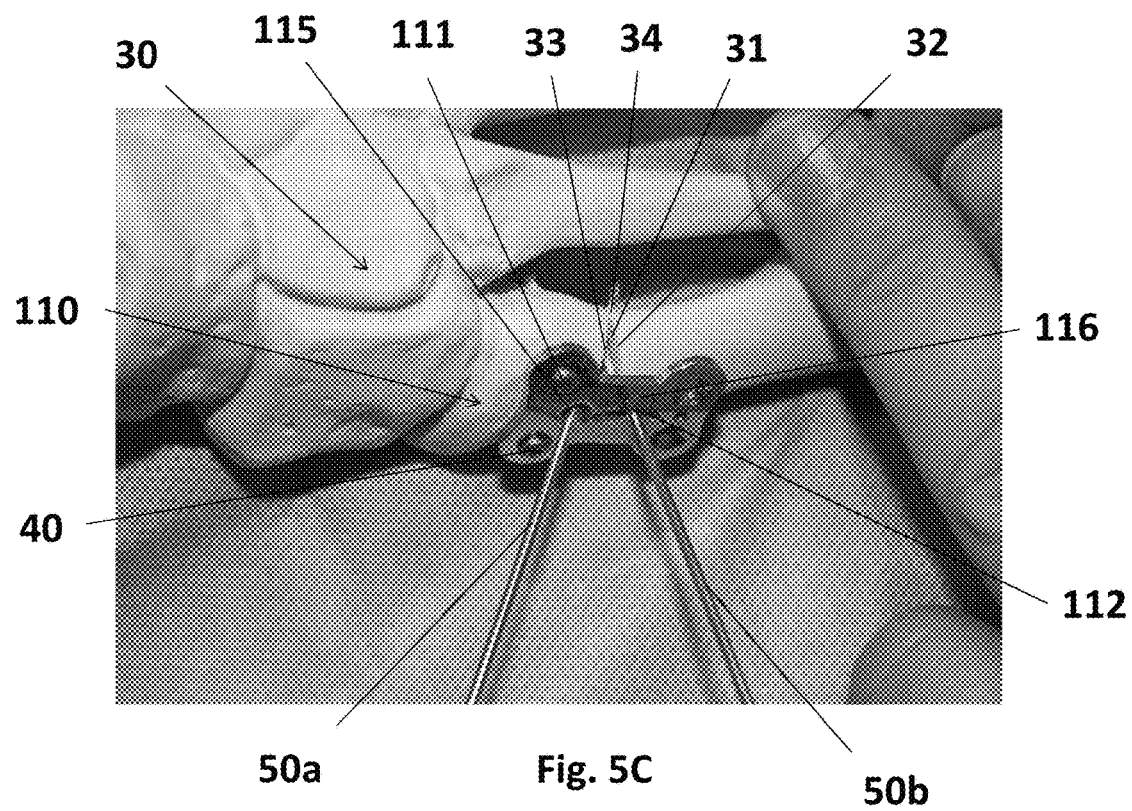
FIG. 5C is a side view of the plate of FIG. 5B after the first and second K-wires have been used to create a gap.

Another exemplary method is illustrated in FIGS. 5A-5C, wherein a bone plate 110 is secured to bone 30. Track 112 of plate 110 has been placed over a partial cut 31a formed in bone (FIG. 5A). Unlike plate 10, bone plate 110 has a plurality of hatch marks 116 disposed along the length of track 112 (FIGS. 5B and 1D). Accordingly, this method further comprises placing bone plate 110 adjacent the bone 30 and aligning one of hatch marks 116 with a face of partial osteotomy cut 31a. For example, once first K-wire 50a has been at least partially inserted into bone 30, then the interior surfaces of conical hole 115 are slid along K-wire 50a until bone plate 110 is placed on bone 30 so as to align one of the marks 116 with cut 31a (FIG. 5A). A next step comprises inserting second K-wire 50b into cut 31a through track 112 at a point adjacent the aligned mark 116 (FIG. 5B), and using the first and second K-wires 50a and 50b as levers to produce an osteotomy gap 31 of a particular width (FIG. 5C). The interval between each of the marks 116 may be measurable in inches or millimeters. Accordingly, this method further comprises moving the second K-wire 50b within track 112 until the second face 33 of the gap 31 is aligned with another one of the marks 116. If positioned parallel to second face 33, as preferred, then second K-wire 50b may also be aligned with one of the marks 116. If used in this method, any edge or surface of body 23 of wedge implant 20 might also be aligned with any set of marks 116.

In some embodiments, the relativity provided by marks 116 permits selection of a wedge implant 20 having a wedge body 23 sized to fit a particular gap 31. For example, another method step comprises selecting, from a kit having plurality of wedge implants 20, a particular wedge implant 20 with a wedge body 23 having a width equal to the width of gap 31. Marks 116 need not be measured or evenly spaced apart to provide this benefit. For example, each mark 116 is spaced apart by an irregular distance equal to the incremental size variations of between each wedge body 23. In lieu of measurements, each implant 20 in this alternative embodiment may be, for example, coded to indicate size. Marks 116 may thus be used to rapidly facilitate the selection of wedge 20 based upon solely upon said coding. Each of wedge 20 or marks 116 may, for example, be color coded. Although described with reference to wedge 20, it should be appreciated that any of these methods may be used with an implant of any size or shape relative to gap 31.

Figure 6A:
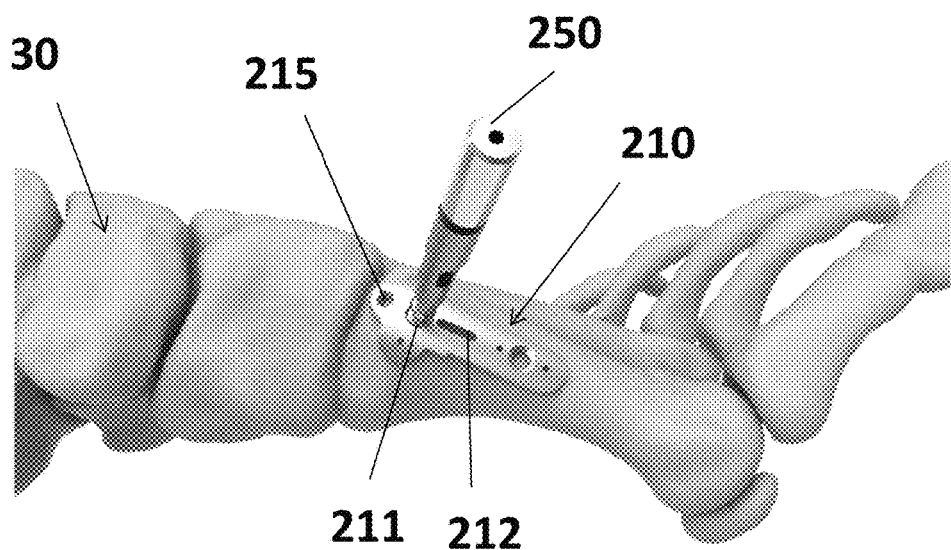
FIG. 6A is a perspective view of the bone plate of FIG. 1E after it has been attached to a joystick and placed on a bone.
Figure 6B:
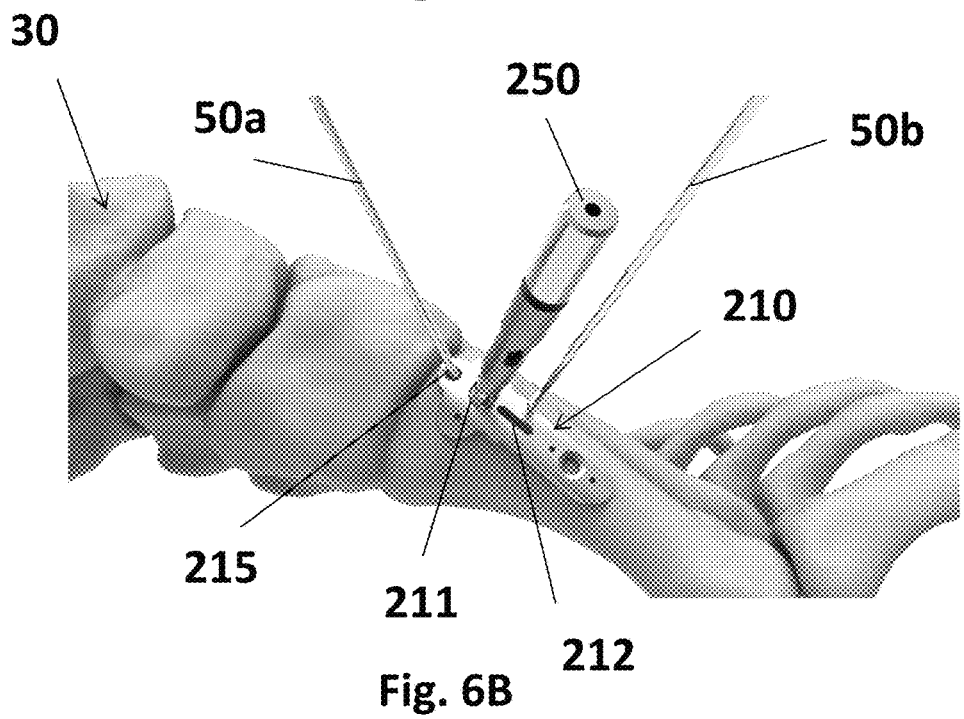
FIG. 6B is a perspective view of the bone of FIG. 6A after a first K-wire has been inserted therethrough and a second K-wire is placed nearby.
Figure 6C:
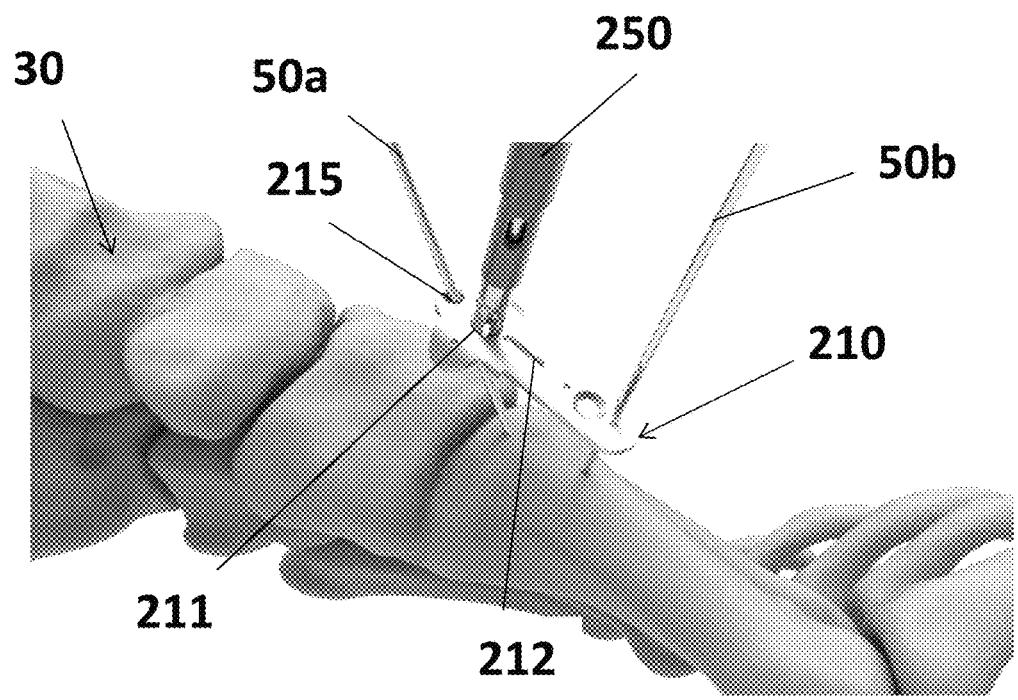
FIG. 6C is a perspective view of the bone plate of FIG. 6B as it is removed from the bone.

Another exemplary set of methods are illustrated in FIGS. 6A through 6H, which sequentially depict various steps for securing bone plate 210 and wedge implant 20 to a bone 30. In a method according to FIGS. 6A-C, bone plate 210 is used as a guiding template for making partial cut 31a. The method comprises attaching bone plate 210 to a joystick 250, and using joystick 250 to place plate 210 on bone 30. For example, an end of joystick 250 is inserted through one of the holes 211 in plate 210 and attached thereto (FIG. 6A). Further steps comprise inserting the first K-wire 50a into a portion of bone 30 through conical hole 215 so as to fix the position of plate 210 on bone (FIG. 6B). Preferably, K-wire 50a is only partially inserted into bone 30 during this step. By way of example, K-wire 50a may be inserted a few millimeters into bone 30, which is just enough to hold plate 210 in a fixed position. With plate 210 fixed, a further step comprises marking bone 30 to indicate the desired location of partial cut 31a. In FIG. 6B, bone 30 is marked by inserting second K-wire 50b into a portion of bone 30 adjacent the track 212 of plate 210. K-wire 50b may alternatively be inserted in track 212 to mark bone 30. In still other embodiments, a pen may be used to mark bone 30. Once the desired location of partial cut 31a has been marked, then this method further comprises using joystick 250 to move plate 210 away from bone 30 (FIG. 6C). At this point, bone 30 is ready to be partially cut at the marked location.

Figure 6D:
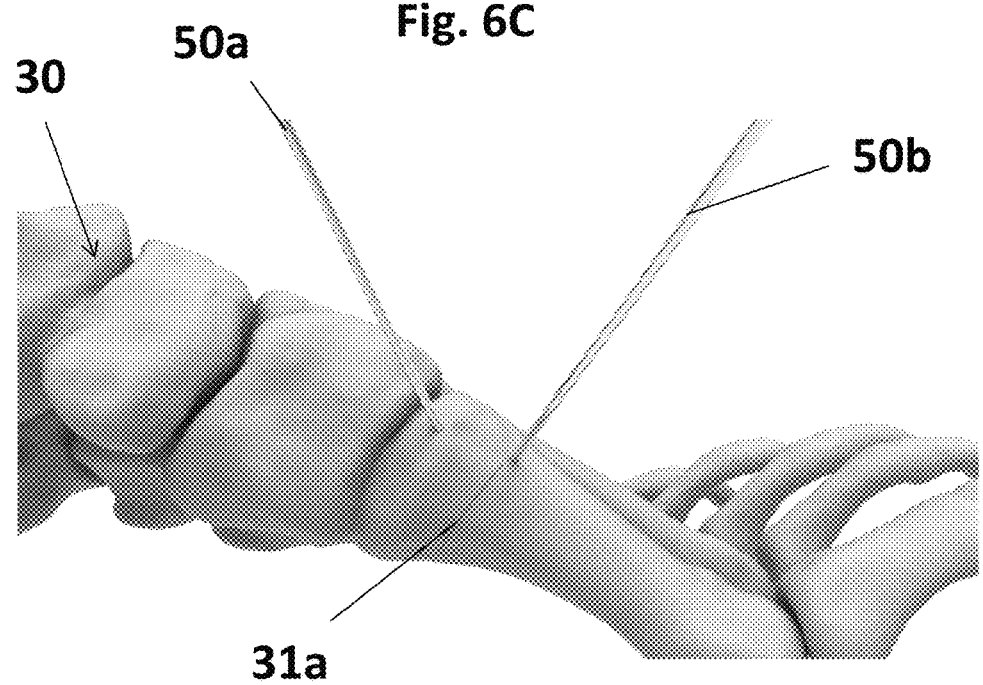
FIG. 6D is a perspective view of the bone of FIG. 6C after a partial cut has been formed therein.
Figure 6E:
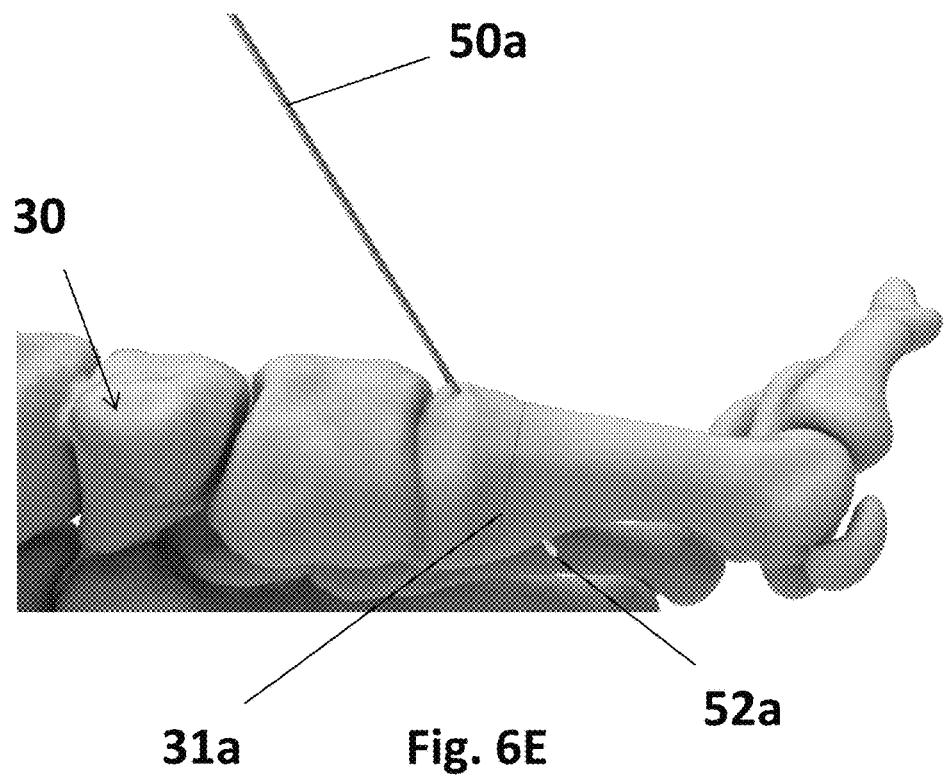
FIG. 6E is a perspective view of the bone of FIG. 6D after the second K-wire has been removed.
Figure 6F:
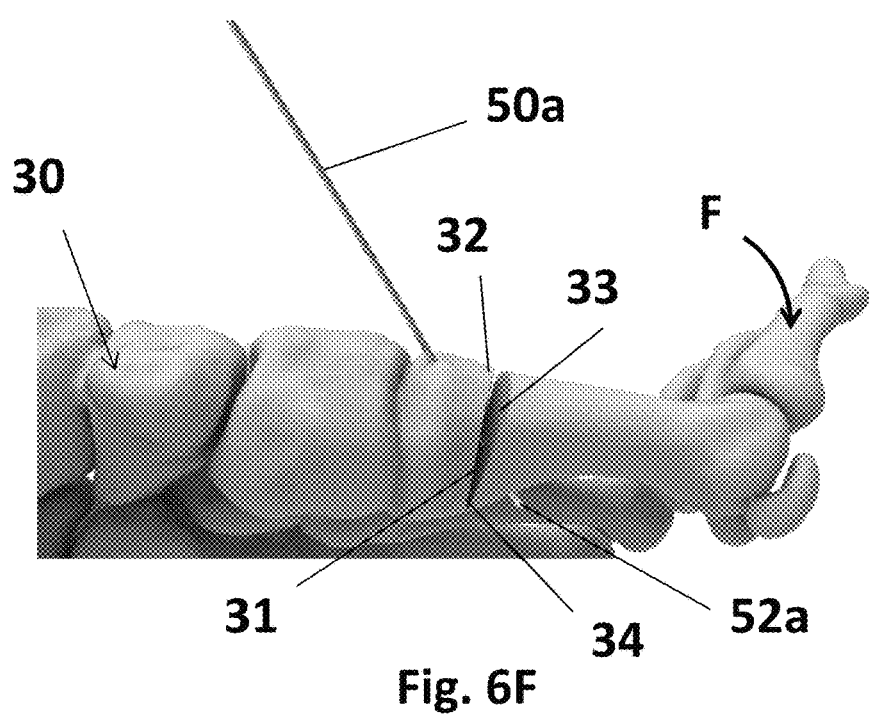
FIG. 6F is a perspective view of the bone of FIG. 6E after the partial cut has been spread open by form a gap.

In a method according to FIGS. 6D-F, first and second K-wires 50a and 50b are used as levers to form osteotomy gap 31 without the guidance of track 212. One step comprises forming partial cut 31a in bone 30 along the outer edge of second K-wire 50b so that cut 31a is substantially parallel with K-wire 50b (FIG. 6D). A next step comprises removing second K-wire 50b from bone 30. With partial cut 31a formed, first K-wire 50a may be fully inserted into bone 30. For example, another step comprise inserting the first K-wire 50a into bone 30 along an insertion axis $K_1$-$K_1$ until the distal end 52A of K-wire 50a is passed across partial cut 31a (FIG. 6E). In this configuration, first K-wire 50a crosses cut 31a so as to capture the opposite distal cortex of the bone 30, thereby reinforcing hinge 34 during and after formation of gap 31. The distal end 52A of first K-wire 50a passes entirely through bone 30 in FIG. 6E.

Gap 31 is formed once hinge 34 has been reinforced by K-wire 50a. In some embodiments, gap 31 is formed by applying a force F (FIG. 6F) to bone 30 that spreads open the partial cut 31a, thereby forming gap 31 from cut 31a. In other embodiments, partial cut 31a is performed on a portion of bone 30 and subsequently opened using another tool (e.g., an osteotome) to produce gap 31. Second K-wire 50b may also be used to form gap 31 as described above.

Figure 6G:
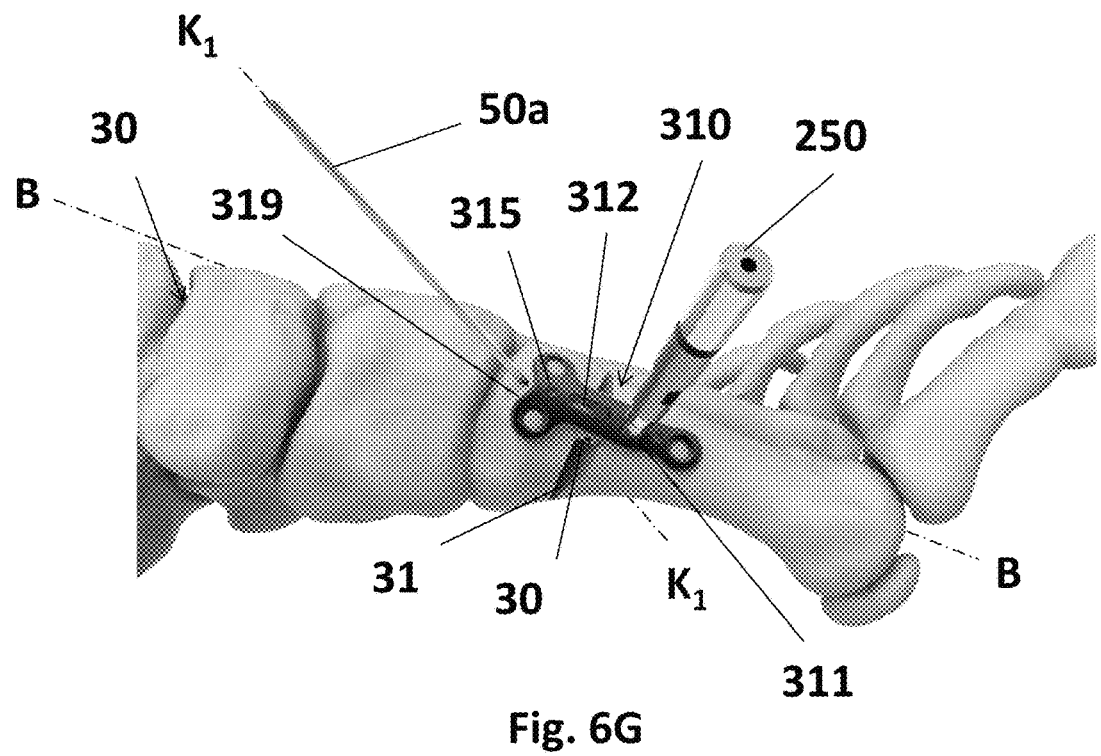
FIG. 6G is a perspective view of bone of FIG. 6F after the wedge implant of FIG. 2A has been engaged with the bone plate of FIG. 1E and placed in the gap.
Figure 6H:
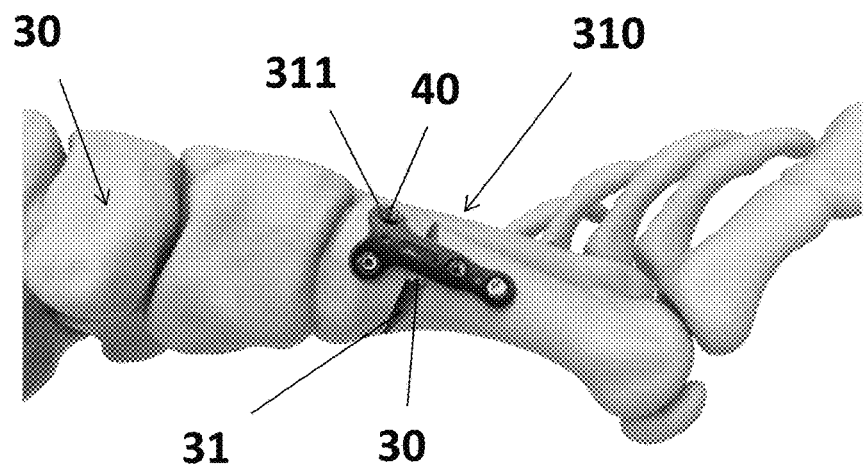
FIG. 6H is a perspective view of the bone FIG. 6G after the construct of FIG. 6G has been secured thereto.

In a set of methods according to FIGS. 6G-H, a bone plate 310 and wedge 20 are secured to bone 30 after gap 31 has been formed from partial cut 31a. Bone plate 310 is similar to plate 210, but for the addition of a K-wire guide portion 319 on one end of plate 310. As shown, guide portion 319 is a valley dimensioned to accommodate a portion of first K-wire 50b. One method step comprises engaging wedge implant 20 with plate 310. Intermediate steps comprise selecting a wedge implant 20 having a wedge body 23 sized to fill gap 31, and passing the engagement portion of implant 20 through track 312 of bone plate 310. A further step comprises using joystick 250 to move plate 310 and wedge implant 20 towards gap 31 and insert wedge body 23 between the first and second faces 32 and 33 of gap 31 (FIG. 6G). In some embodiments, guide portion 319 is placed adjacent first K-wire 50b so that plate 310 and implant 20 may be slid along first K-wire 50b towards gap 31. Preferably, wedge body 23 is sized to fill the gap 31 without damaging hinge 34.

Once wedge body 23 has been placed in gap 31, then another step comprises moving plate 310 relative to wedge implant 20 in order to find the optimal position of bone securement. Once optimally positioned, then plate 310 is, for example, secured to bone 30 by the inserting a screw 40 into each hole 11 (FIG. 6H). In some embodiments, this method may further comprising inserting a locking element, similar to locking element 129 in FIG. 2D, between the divided portions of the head 21 and stem 22 to fix the position of wedge 20 relative to plate 310. This locking element may be inserted before or after plate 310 is secured to bone 30.

An alternative method according to FIGS. 6G-H may comprise selecting a wedge implant 20 that corresponds to the size of osteotomy gap 31. For example, a plurality of wedge implants 20 may be provided in a kit, from which a particular wedge implant 20 is selected to fill gap 31. Another step may comprise inserting the selected implant 20 into said gap 31, preferably without the bone plate 310 attached thereto. For example, wedge body 23 may be inserted into gap 31 such that the engagement portion of implant 20, like head 21 and stem 22 (FIGS. 2A-E), protrudes from the osteotomy gap 31. This configuration allows the plate 310 to be engaged with wedge implant 20 after it has been inserted into gap 31. Accordingly, a next step may comprise placing track 312 over wedge implant 20 and passing the engagement portion of implant 20 through the track so as to moveably engage wedge implant 20 with bone plate 310. Bone plate 310 may now be moved, for example, slid and rotated, relative to the wedge 20. Therefore, this method may further comprise the steps of moving plate 310 relative to wedge 20 in order to find an optimal position for bone securement, and securing plate 310 to the bone 30 by inserting a screw 40 through each hole 311. A locking element may be used to fix the position of wedge 20 relative to plate 310, as above.

FIGS. 6G and 6H also show another alternative method, in which the bone plate 310 and wedge implant 20 are secured to a bone 30 using the first K-wire 50a. This method may comprise the initial step of passing the engagement portion of wedge implant 20 through track 312 so as to moveably engage wedge body 23 with plate 310. A next step may comprise inserting first K-wire 50a through one of the conical holes 315 after the plate 310 has been engaged with the wedge implant 20, and sliding the interior surfaces of hole 315 along first K-wire 50a until it is positioned at an optimal position for bone securement. For example, first K-wire 50a may be inserted in bone 30 along an insertion axis $K_1$-$K_1$ that is oblique to longitudinal axis B-B of the bone 30 until a portion of K-wire 50a spans across osteotomy gap 31 (e.g., FIG. 4C). At this point, because first K-wire 50a is sticking out of bone 30, the tapered interior surfaces of conical hole 311 may be used to guide plate 310 and wedge implant 20 towards bone 30.

Certain elements of the present invention, such as first and second K-wires 50a and 50b, have been described in relation to a particular opening in an embodiment of the bone plate 10, such as conical hole 15. Any K-wire 50 may alternatively be inserted through any opening in any embodiment of bone plate 10, such as hole 11, hole 15, or track 12. For example, second K-wire 50b, or other additional K-wire, may be inserted through the track 12 and along or through the other of the first or second sides 32, 33 of the gap 31 to further reinforce the hinge 34 of the osteotomy gap 31. In such an exemplary method, the trajectories of the each K-wire 50a and 50b may intersect, thereby reinforcing both sides 32, 33 of the hinge of the osteotomy gap 31. Where necessary, it is further envisioned that either K-wire 50a or 50b may be inserted through the one of the holes 11 or any other available hole or portal of bone plate 10.

A number of kits are also enabled by the disclosure set forth herein. For example, any embodiment of bone plate 10 and wedge implant 20 may be provided in a variety of shapes and sizes. Therefore, it is envisioned that a surgeon, in implementing the present invention, may consider mixing and matching different bone plates 10, 110, 210, etc., with different wedge implants 20, 120, 220, etc., in order to obtain the most optimal placement in gap 31. Thus, by using a kit according to the present invention, the surgeon may choose, from a plurality of bone plates 10 and wedge implants 20, a particular bone plate 10 which most closely fits against the bone 30, as well as a particular wedge implant 20 which most closely fits within the osteotomy gap 31. Each wedge implant 20 in such a kit preferably has engagement portion that is interchangeably engageable with any embodiment of bone plate 10 as described herein. A plurality of screws 40 and locking elements 129 may also be included. Each wedge body 20 in an exemplary kit may be coded to indicate its size relative to gap 31 or a set of marks 116 on any embodiment of bone plate 10. Accordingly, it is also envisioned that such kits may be also used with a medical procedure other than an osteotomy may necessitate an unconventional cut (i.e., not wedge-shaped), in which case the surgeon may perform the required cut and then choose the closest and most appropriate wedge implant 20 from said kit to fit the resultant space.

Although the invention herein has been described with reference to particular embodiments, it is to be understood that these embodiments are merely illustrative of the principles and applications of the present invention. It is to be understood unless otherwise indicated herein that the figures are not intended to be to scale. It is therefore to be understood that numerous modifications may be made to the illustrative embodiments and that other arrangements may be devised without departing from the spirit and scope of the present invention as defined by the appended paragraphs.

The invention claimed is:

1. An implant comprising:
a plate having a track and a plurality of holes; and
a wedge body having an engagement portion that is passed through the track so as to moveably engage the wedge body with the plate, wherein at least a portion of the engagement portion is narrowed while passing through the track,
wherein the engagement portion comprises a first engagement portion and a second engagement portion, each engagement portion being movable towards the other.

2. The implant of claim 1, wherein the first and second engagement portions are moved away from each other after passing through the track.

3. The implant of claim 1, further comprising an aperture extending through the engagement portion and a portion of the wedge body so as to define the first and second engagement portions.

4. The implant of claim 3, wherein the aperture forms a living hinge in the wedge body.

5. The implant of claim 4, wherein the living hinge biases the first and second engagement portions away from each other after passing through the track.

6. A kit comprising:
a plurality of implants according to claim 1,
each implant having a wedge body that is moveably engageable with at least one of the plates.

7. The kit of claim 6, wherein at least a first wedge body of the plurality of implants is sized differently than a second wedge body of the plurality of implants.

8. An implant comprising:
a bone plate having a track; and
a wedge body having an engagement portion that is passed through the track so as to moveably engage the wedge body with the bone plate,
wherein the engagement portion comprises a head with a stem connected to the wedge body, each of the head and stem being adapted to pass through the track, and
wherein at least a portion of the head is formed of a compressible material that is configured to be compressed while passing through the track.

9. The implant of claim 8, wherein the head and stem are rotatably engageable with the track.

10. The implant of claim 8, wherein the head and the stem are split into at least two divided portions, each divided portion being movable relative to the other divided portion while passing through the track.

11. The implant of claim 10, wherein an exterior surface of each of the at least two divided portions is adapted to apply a biasing force against an interior surface of track.

12. The implant of claim 11, wherein an interior surface of each of the at least two divided portions has a semi-circular portion that defines a split bore when the wedge body is engaged with the plate.

13. The implant of claim 12, further comprising a locking element inserted into the split bore to fix the position of the wedge body relative to bone plate.

14. The implant of claim 11, further comprising a plurality of hatch marks on the bone plate, each mark incrementally denoting a length measurement.

15. An implant comprising:
a bone plate having at least one track; and
a wedge body having:
an engagement portion including a head attached to the wedge body by a stem; and
at least one aperture extending through the engagement portion so as to split the head and stem into at least two divided portions, each divided portion being resiliently movable relative to the other when passed through the track so as to movably engage the wedge body with the bone plate.

16. The implant of claim 15, wherein an interior surface of each of the at least two divided portions defines one half of a split bore adapted to receive a locking element that fixes the position of the wedge body relative to the plate.

17. The implant of claim 16, wherein the locking element is a screw and at least a semi-circular portion of the interior surface is constructed from a softer material than the screw.

18. An implant comprising:
a bone plate having a first side and a second side and having a track formed through the first and second sides; and
a wedge body having an engagement portion that is passed through the track so as to moveably engage the wedge body with the bone plate,
wherein the engagement portion comprises a head with a stem connected to the wedge body, each of the head and stem being adapted to pass through the track, and
wherein the head and the stem are adapted to pass through the bone plate between the first side and the second side at a first end of a length of the track and at a second end of the length of the track, the length extending between the first end and the second end.

* * * * *